(12) United States Patent  
Nishiyama et al.

(10) Patent No.: US 8,982,204 B2  
(45) Date of Patent: Mar. 17, 2015

(54) INSPECTION MANAGEMENT APPARATUS, SYSTEM, AND METHOD, AND COMPUTER READABLE RECORDING MEDIUM

(71) Applicant: Olympus Medical Systems Corp., Tokyo (JP)

(72) Inventors: Takeshi Nishiyama, Kawasaki (JP); Isao Tateshita, Chofu (JP); Keiji Okumura, Tokyo (JP); Takaharu Hosoi, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/258,180

(22) Filed: Apr. 22, 2014

(65) Prior Publication Data

US 2014/0300719 A1    Oct. 9, 2014

Related U.S. Application Data

(63) Continuation of application No. PCT/JP2013/078853, filed on Oct. 24, 2013.

(30) Foreign Application Priority Data

Oct. 24, 2012 (JP) ................................. 2012-235157

(51) Int. Cl.  
*A61B 1/00* (2006.01)  
*H04N 5/92* (2006.01)  
(Continued)

(52) U.S. Cl.  
CPC ............. *A61B 1/00009* (2013.01); *A61B 1/041* (2013.01); *G06F 19/321* (2013.01); *A61B 1/0002* (2013.01); *H04N 5/92* (2013.01)  
USPC ........................................................ 348/74

(58) Field of Classification Search  
CPC ............... A61B 1/00016; A61B 1/041; A61B 1/00009; A61B 1/0002; H04N 5/92; G06F 19/321  
USPC ............................................................ 348/74  
See application file for complete search history.

(56) References Cited

U.S. PATENT DOCUMENTS 8,382,658 B2 *   2/2013   Shigemori ..................... 600/103  
8,711,205 B2 *   4/2014   Takasugi et al. ................ 348/45  
(Continued)

FOREIGN PATENT DOCUMENTS

JP    2008-178703 A    8/2008  
JP    2010-165109 A    7/2010  
(Continued)

OTHER PUBLICATIONS

Decision of a Patent Grant dated Jun. 3, 2014 received in related Japanese Application No. 2014-514984.

(Continued)

*Primary Examiner* — Jay Patel  
*Assistant Examiner* — Frank Huang  
(74) *Attorney, Agent, or Firm* — Scully, Scott, Murphy & Presser, PC

(57) ABSTRACT

An inspection management apparatus includes: a schedule generation unit that, based on a scheduled start date and time of examination, a scheduled start date and time of observation, a predictive transfer time of image data from a receiving device to an inspection management apparatus, and a predictive image processing time for each type of image processing, calculates an image transfer start date and time from the receiving device to the inspection management apparatus, and calculates an image processing start date and time of the transferred image data; and a control unit that starts acquisition of the image data transmitted from the receiving device when the image transfer start date and time comes, and causes, when the image processing start date and time comes, an image processing unit to perform specified image processing on the image data that the transfer has been started on the image transfer start date and time.

20 Claims, 27 Drawing Sheets

(51) Int. Cl.
*A61B 1/04* (2006.01)
*G06F 19/00* (2011.01)

(56) References Cited

U.S. PATENT DOCUMENTS

| | | | |
|---|---|---|---|
| 8,854,444 B2* | 10/2014 | Kobayashi et al. | 348/65 |
| 2004/0242962 A1* | 12/2004 | Uchiyama | 600/118 |
| 2007/0177075 A1* | 8/2007 | Kimoto | 349/110 |
| 2013/0158344 A1 | 6/2013 | Taniguchi | |

FOREIGN PATENT DOCUMENTS

| | | |
|---|---|---|
| JP | 5238100 B2 | 4/2013 |
| WO | WO 2012/137705 A1 | 10/2012 |

OTHER PUBLICATIONS

International Search Report dated Nov. 26, 2013 from related International Application No. PCT/JP2013/078853.

* cited by examiner

FIG.5

| TYPE CODE OF OBSERVATION PURPOSE | TYPE OF OBSERVATION PURPOSE | TARGET IMAGE | TYPE OF IMAGE PROCESSING |
|---|---|---|---|
| 001 | LESION IMAGE OBSERVATION | ENTIRE IMAGE | LESION DETECTION PROCESS |
| 002 | REPRESENTATIVE IMAGE OBSERVATION | ENTIRE IMAGE | REPRESENTATIVE IMAGE EXTRACTION PROCESS |
| 003 | ENTIRE IMAGE OBSERVATION | ENTIRE IMAGE | SIMILAR IMAGE DETECTION PROCESS, RED DETECTION PROCESS, POSITION DETECTION PROCESS |
| 004 | CAPTURED AREA OBSERVATION | ENTIRE IMAGE | SIMILAR IMAGE DETECTION PROCESS |
| 005 | LESION IMAGE OBSERVATION FOR ESOPHAGUS | ESOPHAGUS IMAGE | ORGAN DISCRIMINATION PROCESS, LESION DETECTION PROCESS |
| 006 | LESION IMAGE OBSERVATION FOR STOMACH | STOMACH IMAGE | ORGAN DISCRIMINATION PROCESS, LESION DETECTION PROCESS |
| 007 | LESION IMAGE OBSERVATION FOR SMALL INTESTINE | SMALL INTESTINE IMAGE | ORGAN DISCRIMINATION PROCESS, LESION DETECTION PROCESS |
| 008 | LESION IMAGE OBSERVATION FOR LARGE INTESTINE | LARGE INTESTINE IMAGE | ORGAN DISCRIMINATION PROCESS, LESION DETECTION PROCESS |
| 009 | REPRESENTATIVE IMAGE OBSERVATION FOR ESOPHAGUS | ESOPHAGUS IMAGE | ORGAN DISCRIMINATION PROCESS, REPRESENTATIVE IMAGE EXTRACTION PROCESS |
| 010 | REPRESENTATIVE IMAGE OBSERVATION FOR STOMACH | STOMACH IMAGE | ORGAN DISCRIMINATION PROCESS, REPRESENTATIVE IMAGE EXTRACTION PROCESS |
| 011 | REPRESENTATIVE IMAGE OBSERVATION FOR SMALL INTESTINE | SMALL INTESTINE IMAGE | ORGAN DISCRIMINATION PROCESS, REPRESENTATIVE IMAGE EXTRACTION PROCESS |
| 012 | REPRESENTATIVE IMAGE OBSERVATION FOR LARGE INTESTINE | LARGE INTESTINE IMAGE | ORGAN DISCRIMINATION PROCESS, REPRESENTATIVE IMAGE EXTRACTION PROCESS |
| 013 | ENTIRE IMAGE OBSERVATION FOR ESOPHAGUS | ESOPHAGUS IMAGE | ORGAN DISCRIMINATION PROCESS, SIMILAR IMAGE DETECTION PROCESS |
| 014 | ENTIRE IMAGE OBSERVATION FOR STOMACH | STOMACH IMAGE | ORGAN DISCRIMINATION PROCESS, SIMILAR IMAGE DETECTION PROCESS |
| 015 | ENTIRE IMAGE OBSERVATION FOR SMALL INTESTINE | SMALL INTESTINE IMAGE | ORGAN DISCRIMINATION PROCESS, SIMILAR IMAGE DETECTION PROCESS |
| 016 | ENTIRE IMAGE OBSERVATION FOR LARGE INTESTINE | LARGE INTESTINE IMAGE | ORGAN DISCRIMINATION PROCESS, SIMILAR IMAGE DETECTION PROCESS |

FIG.6

| COMMU-NICATION METHOD | AVERAGE VALUE [SEC-ONDS/IMAGE] | MAXIMUM VALUE [SEC-ONDS/IMAGE] | MINIMUM VALUE [SEC-ONDS/IMAGE] | MODE VALUE [SEC-ONDS/IMAGE] | MEDIAN VALUE [SEC-ONDS/IMAGE] |
|---|---|---|---|---|---|
| USB | 0.0060 | 0.0080 | 0.0050 | 0.0070 | 0.0060 |
| WIRELESS LAN | 0.0050 | 0.0090 | 0.0040 | 0.0060 | 0.0050 |
| MOBILE PHONE LINE | 0.0100 | 0.0120 | 0.0090 | 0.0110 | 0.0100 |
| INTEGRATION | 0.0080 | 0.0100 | 0.0070 | 0.0090 | 0.0080 |

FIG.7

| TYPE OF IMAGE PROCESSING | AVERAGE VALUE [SECONDS/ IMAGE] | MAXIMUM VALUE [SECONDS/ IMAGE] | MINIMUM VALUE [SECONDS/ IMAGE] | MODE VALUE [SECONDS/ IMAGE] | MEDIAN VALUE [SECONDS/ IMAGE] |
|---|---|---|---|---|---|
| LESION DETECTION PROCESS | 0.010 | 0.020 | 0.008 | 0.015 | 0.010 |
| REPRESENTATIVE IMAGE DETECTION PROCESS | 0.020 | 0.030 | 0.018 | 0.025 | 0.020 |
| SIMILAR IMAGE DETECTION PROCESS | 0.020 | 0.030 | 0.018 | 0.025 | 0.020 |
| RED DETECTION PROCESS | 0.010 | 0.020 | 0.008 | 0.015 | 0.010 |
| POSITION DETECTION PROCESS | 0.030 | 0.040 | 0.028 | 0.035 | 0.030 |
| ORGAN DETECTION PROCESS | 0.020 | 0.030 | 0.018 | 0.025 | 0.020 |

FIG.8

| EXAMINATION IDENTIFICATION CODE | USB | | WIRELESS LAN | | MOBILE PHONE LINE | |
|---|---|---|---|---|---|---|
| | NUMBER OF IMAGES | IMAGE TRANSFER TIME [SEC] | NUMBER OF IMAGES | IMAGE TRANSFER TIME [SEC] | NUMBER OF IMAGES | IMAGE TRANSFER TIME [SEC] |
| 0000001 | 60000 | 700 | 0 | 0 | 0 | 0 |
| 0000002 | 50000 | 600 | 30000 | 300 | 0 | 0 |
| 0000003 | 40000 | 500 | 10000 | 100 | 10000 | 300 |
| ⋮ | ⋮ | ⋮ | ⋮ | ⋮ | ⋮ | ⋮ |

FIG.9

| PERIOD OF TIME | COMMUNI-CATION METHOD | MONDAY | | | | | ... |
| --- | --- | --- | --- | --- | --- | --- | --- |
| | | AVER-AGE VALUE [SEC-ONDS/IMAGE] | MAXIMUM VALUE [SEC-ONDS/IMAGE] | MINIMUM VALUE [SEC-ONDS/IMAGE] | MODE VALUE [SEC-ONDS/IMAGE] | MEDIAN VALUE [SEC-ONDS/IMAGE] | ... |
| 8:00 TO 8:15 | USB | 0.0060 | · | · | · | 0.0060 | ... |
| | WIRELESS LAN | 0.0050 | · | · | · | 0.0050 | ... |
| | MOBILE PHONE LINE | 0.0100 | · | · | · | 0.0100 | ... |
| | INTEGRA-TION | 0.0080 | · | · | · | 0.0080 | ... |
| 8:15 TO 8:30 | ... | ... | · | · | · | ... | ... |
| ⋮ | ⋮ | ⋮ | ⋮ | ⋮ | ⋮ | ⋮ | ⋮ |

FIG.10

| EXAMI-NATION IDENTIFI-CATION CODE | LESION DETECTION PROCESS | | REPRESENTATIVE IMAGE DETECTION PROCESS | | ... | ... |
| --- | --- | --- | --- | --- | --- | --- |
| | NUMBER OF TARGET IMAGES | PROC-ESSING TIME [SEC] | NUMBER OF TARGET IMAGES | PROC-ESSING TIME [SEC] | | |
| 0000001 | 60000 | 666 | 60000 | 0 | ... | ... |
| 0000002 | 80000 | 888 | 80000 | 333 | ... | ... |
| 0000003 | 70000 | 777 | 70000 | 111 | ... | ... |
| ⋮ | ⋮ | ⋮ | ⋮ | ⋮ | ⋮ | ⋮ |

FIG.11

| PERIOD OF TIME | TYPE OF IMAGE PROCESSING | MONDAY | | | | | ... |
| --- | --- | --- | --- | --- | --- | --- | --- |
| | | AVER-AGE VALUE [SEC-ONDS/IMAGE] | MAXIMUM VALUE [SEC-ONDS/IMAGE] | MINIMUM VALUE [SEC-ONDS/IMAGE] | MODE VALUE [SEC-ONDS/IMAGE] | MEDIAN VALUE [SEC-ONDS/IMAGE] | ... |
| 8:00 TO 8:15 | LESION DETECTION PROCESS | 0.010 | · | · | · | 0.010 | ... |
| | REPRESENT-ATIVE IMAGE DETECTION PROCESS | 0.010 | · | · | · | 0.010 | ... |
| | SIMILAR IMAGE DETECTION PROCESS | 0.020 | · | · | · | 0.020 | ... |
| | RED DETECTION PROCESS | 0.010 | · | · | · | 0.010 | ... |
| | POSITION DETECTION PROCESS | 0.030 | · | · | · | 0.030 | ... |
| 8:15 TO 8:30 | ... | ... | · | · | · | ... | ... |
| ⋮ | ⋮ | ⋮ | ⋮ | ⋮ | ⋮ | ⋮ | ⋮ |

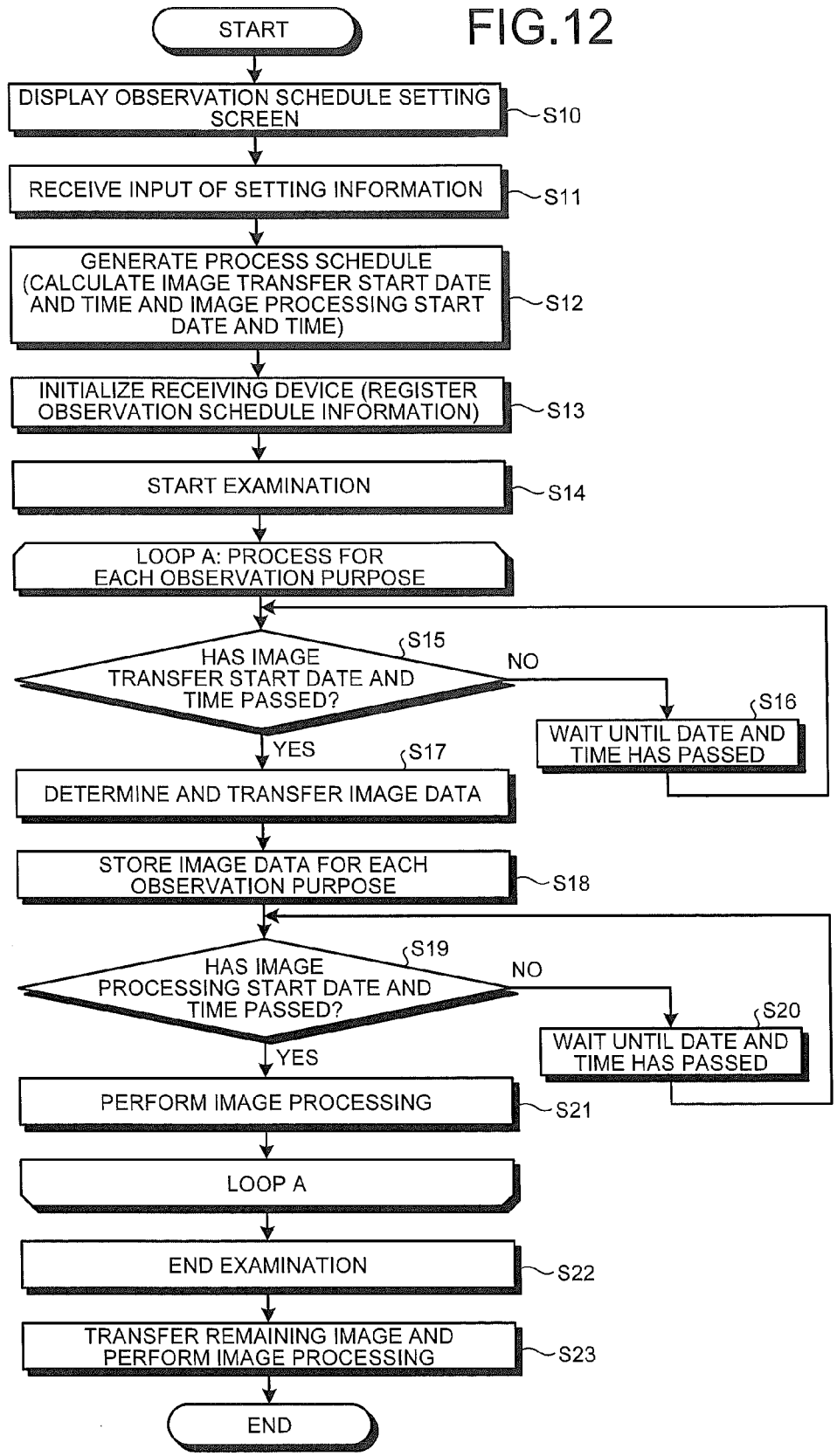

FIG.13

| NUM-BER | PA-TIENT NAME | SCHEDULED SWALLOWING DATE AND TIME | SCHEDULED START DATE AND TIME OF OBSERVATION | OBSERVATION PURPOSE | DOCTOR NAME |
|---|---|---|---|---|---|
| 1 | ZZZ | 2012.2.3 10:15 | 2012.2.3 11:55 | LESION IMAGE OBSERVATION FOR ESOPHAGUS ▼ | SSS |
| 2 | ZZZ | 2012.2.3 10:15 | 2012.2.3 14:25 | LESION IMAGE OBSERVATION FOR STOMACH ▼ | SSS |
| 3 | ZZZ | 2012.2.3 10:15 | 2012.2.3 17:30 | REPRESENTATIVE IMAGE OBSERVATION ▼ | SSS |
| 4 | ZZZ | 2012.2.3 10:15 | 2012.2.3 19:00 | ENTIRE IMAGE OBSERVATION ▼ | SSS |
| 5 | YYY | 2012.2.3 10:30 | 2012.2.3 17:40 | REPRESENTATIVE IMAGE OBSERVATION ▼ | SSS |
| 6 | YYY | 2012.2.4 10:30 | 2012.2.4 10:00 | ENTIRE IMAGE OBSERVATION ▼ | SSS | m11  m12  m13  m14  m15  m16

FIG.14

| SCHEDULED SWALLOWING DATE AND TIME | SCHEDULED START DATE AND TIME OF OBSERVATION | NUMBER OF IMAGES FOR TIME CALCULATION | TYPE OF OBSERVATION PURPOSE | AVERAGE VALUE OF IMAGE PROCESSING NECESSARY TIME [SECONDS/IMAGE] | IMAGE PROCESSING TIME [SEC] | IMAGE PROCESSING START DATE AND TIME | AVERAGE VALUE OF IMAGE TRANSFER NECESSARY TIME [SECONDS/IMAGE] | IMAGE TRANSFER TIME [SEC] | IMAGE TRANSFER START DATE AND TIME |
|---|---|---|---|---|---|---|---|---|---|
| 2012.2.3 10:15 | 2012.2.3 11:55 | 12000 | LESION IMAGE OBSERVATION FOR ESOPHAGUS | 0.030 | 360 | 2012.2.3 11:49 | WIRELESS LAN 0.0050 | 60 | 2012.2.3 11:48 |
| | 2012.2.3 14:25 | ⋮ | LESION IMAGE OBSERVATION FOR STOMACH | 0.030 | ⋮ | ⋮ | WIRELESS LAN 0.0050 | ⋮ | ⋮ |
| | 2012.2.3 17:30 | ⋮ | REPRESENTATIVE IMAGE OBSERVATION | 0.010 | ⋮ | ⋮ | WIRELESS LAN 0.0050 | ⋮ | ⋮ |
| | 2012.2.3 19:00 | ⋮ | ENTIRE IMAGE OBSERVATION | 0.060 | ⋮ | ⋮ | WIRELESS LAN 0.0050 | ⋮ | ⋮ |
| ← m21 | ← m22 | ← m24 | ← m23 | ← m25 | ← m26 | ← m27 | ← m28 | ← m29 | ← m30 |

M2

| NUM-BER | IMAGE TRANSFER START DATE AND TIME | TARGET IMAGE |
|---|---|---|
| 1 | 2012.2.3 11:48 | ESOPHAGUS IMAGE |
| 2 | 2012.2.3 14:25 | STOMACH IMAGE |
| 3 | 2012.2.3 17:30 | ENTIRE IMAGE |
| 4 | 2012.2.3 19:00 | ENTIRE IMAGE |

FIG.18

| NUM-BER | PA-TIENT NAME | SCHEDULED SWALLOWING DATE AND TIME | SCHEDULED DATE AND TIME OF PATIENT REVISIT | SCHEDULED START DATE AND TIME OF OBSERVATION | OBSERVATION PURPOSE | DOCTOR NAME |
|---|---|---|---|---|---|---|
| 1 | ZZZ | 2012.2.3 10:15 | 2012.2.3 18:15 | 2012.2.3 11:55 | LESION IMAGE OBSERVATION FOR ESOPHAGUS ▶ | SSS |
| 2 | ZZZ | 2012.2.3 10:15 | 2012.2.3 18:15 | 2012.2.3 14:25 | LESION IMAGE OBSERVATION FOR STOMACH ▶ | SSS |
| 3 | ZZZ | 2012.2.3 10:15 | 2012.2.3 18:15 | 2012.2.3 17:30 | REPRESENTATIVE IMAGE OBSERVATION FOR SMALL INTESTINE ▶ | SSS |
| 4 | ZZZ | 2012.2.3 10:15 | 2012.2.3 18:15 | 2012.2.3 19:00 | ENTIRE IMAGE OBSERVATION ▶ | SSS |
| 5 | YYY | 2012.2.3 10:30 | 2012.2.3 18:30 | 2012.2.3 17:40 | REPRESENTATIVE IMAGE OBSERVATION ▶ | SSS |
| 6 | YYY | 2012.2.4 10:30 | 2012.2.4 18:30 | 2012.2.4 10:00 | ENTIRE IMAGE OBSERVATION ▶ | SSS |

FIG.19

| SCHED-ULED SWAL-LOWING DATE AND TIME | SCHED-ULED DATE AND TIME OF PATIENT REVISIT | SCHED-ULED START DATE AND TIME OF OBSER-VATION | OBSER-VATION PURPOSE | IMAGE PROCES-SING START DATE AND TIME | IMAGE TRANSFER START DATE AND TIME |
|---|---|---|---|---|---|
| 2012.2.3 10:15 | 2012.2.3 18:15 | 2012.2.3 11:55 | LESION IMAGE OB-SERVATION FOR ESOPHAGUS | 2012.2.3 11:49 | 2012.2.3 11:48 |
| | | 2012.2.3 14:25 | LESION IMAGE OB-SERVATION FOR STOMACH | 2012.2.3 14:23 | 2012.2.3 14:22 |
| | | 2012.2.3 17:30 | REPRE-SENTATIVE IMAGE OB-SERVATION FOR SMALL INTESTINE | 2012.2.3 17:10 | 2012.2.3 17:05 |
| | | 2012.2.3 19:00 | ENTIRE IMAGE OB-SERVATION | 2012.2.3 18:50 | 2012.2.3 18:45 |

FIG.20

| NUM-BER | IMAGE TRANSFER START DATE AND TIME | TARGET IMAGE |
|---|---|---|
| 1 | 2012.2.3 11:48 | ESOPHAGUS IMAGE |
| 2 | 2012.2.3 14:25 | STOMACH IMAGE |
| 3 | 2012.2.3 17:30 | SMALL INTESTINE IMAGE |
| 4 | | |

FIG.22

| NUM-BER | PA-TIENT NAME | SCHEDULED SWALLOWING DATE AND TIME | CLIENT WS NAME | SCHEDULED START DATE AND TIME OF OBSERVATION | OBSERVATION PURPOSE | DOCTOR NAME |
|---|---|---|---|---|---|---|
| 1 | ZZZ | 2012.2.3 10:15 | WS_A ▶ | 2012.2.3 11:55 | LESION IMAGE OBSERVATION FOR ESOPHAGUS ▶ | SSS |
| 2 | ZZZ | 2012.2.3 10:15 | WS_A | 2012.2.3 14:25 | LESION IMAGE OBSERVATION FOR STOMACH ▶ | SSS |
| 3 | ZZZ | 2012.2.3 10:15 | WS_A | 2012.2.3 17:30 | REPRESENTATIVE IMAGE OBSERVATION ▶ | SSS |
| 4 | ZZZ | 2012.2.3 10:15 | WS_A | 2012.2.3 19:00 | ENTIRE IMAGE OBSERVATION ▶ | SSS |
| 5 | YYY | 2012.2.3 10:30 | WS_B ▶ | 2012.2.3 17:40 | REPRESENTATIVE IMAGE OBSERVATION ▶ | SSS |
| 6 | YYY | 2012.2.4 10:30 | WS_B | 2012.2.4 10:00 | ENTIRE IMAGE OBSERVATION ▶ | SSS |

| NUM-BER | CLIENT WS IDENTIFICATION INFORMATION | IMAGE TRANSFER START DATE AND TIME | TARGET IMAGE |
|---|---|---|---|
| 1 | WS_A | 2012.2.3 11:48 | ESOPHAGUS IMAGE |
| 2 | WS_A | 2012.2.3 14:25 | STOMACH IMAGE |
| 3 | WS_A | 2012.2.3 17:30 | ENTIRE IMAGE |
| 4 | WS_A | 2012.2.3 19:00 | ENTIRE IMAGE |

| NUM-BER | IMAGE TRANSFER START DATE AND TIME | CLIENT WS NAME | OBSERVATION PURPOSE |
|---|---|---|---|
| 1 | 2012.2.3 11:48 | WS_A | LESION IMAGE OBSERVATION FOR ESOPHAGUS |
| 2 | 2012.2.3 14:22 | WS_A | LESION IMAGE OBSERVATION FOR STOMACH |
| 3 | 2012.2.3 17:05 | WS_A | REPRESENTATIVE IMAGE OBSERVATION |
| 4 | 2012.2.3 18:45 | WS_A | ENTIRE IMAGE OBSERVATION |
| 5 | ⋮ | WS_B | REPRESENTATIVE IMAGE OBSERVATION |
| 6 | ⋮ | WS_B | ENTIRE IMAGE OBSERVATION |

INSPECTION MANAGEMENT APPARATUS, SYSTEM, AND METHOD, AND COMPUTER READABLE RECORDING MEDIUM

CROSS REFERENCES TO RELATED APPLICATIONS

This application is a continuation of PCT international application Ser. No. PCT/JP2013/078853 filed on Oct. 24, 2013 which designates the United States, incorporated herein by reference, and which claims the benefit of priority from Japanese Patent Application No. 2012-235157, filed on Oct. 24, 2012, incorporated herein by reference.

BACKGROUND OF THE INVENTION

1. Field of the Invention

The present invention relates to an inspection management apparatus, an inspection management system, an inspection management method, and a computer readable recording medium, which manage examinations in a capsule endoscopic system using a capsule endoscope that is introduced into a subject and captures images of inside of the subject.

2. Description of the Related Art

In recent years, examinations using capsule endoscopes that are introduced into subjects, such as patients, and capture images of inside of the subjects are known in the field of endoscopes. A capsule endoscope is an apparatus that has a built-in imaging function, a built-in wireless communication function, and the like provided in a casing of a capsule shape formed in a size introducible into a digestive tract of a subject, and after being swallowed via a mouth of the subject, captures images while moving inside the digestive tract by peristaltic movement or the like and generates image data. The capsule endoscope sequentially transmits the generated image data by wireless to outside of the subject.

The image data wirelessly transmitted from the capsule endoscope is received by a receiving device provided outside the subject, and accumulated in a built-in memory or a portable memory. After the examination ends, the image data accumulated in the memory is transferred to a workstation, a server, or the like, and subjected to specified image processing. A medical worker performs diagnosis on the subject by observing the images generated as described above.

Transfer of the image data from the receiving device to the workstation or the like is generally performed such that, after the end of an examination, the receiving device or a portable member removed from the receiving device is set in a reading device connected to the workstation or the like and then the data is read. Alternatively, the image data may be transferred via wireless communication, a mobile phone line, the Internet, or the like. In such a case, the image data may not necessarily have to be transferred after the end of examinations, but may be transferred at various timings, such as immediately after the receiving device has received image data from the capsule endoscope (real time transmission), when a certain amount of image data is accumulated in the receiving device (quantitative transmission), at specified time intervals (periodic transmission), or depending on communication quality, such as a bandwidth or congestion of a communication line.

As a technique related to transfer of image data, Japanese Laid-open Patent Publication No. 2010-165109 discloses a medical image diagnosis apparatus that stores images scanned and generated based on examination appointment information including an observation scheduled date and time, controls transfer queues of the images based on the observation scheduled date and time, and reads and transfers the images from a storage means under control of the transfer queues.

SUMMARY OF THE INVENTION

An inspection management apparatus according to one aspect of the invention is an inspection management apparatus for managing an examination performed in a capsule endoscopic system including a receiving device that receives image data from a capsule endoscope and stores the image data. The inspection management apparatus includes: a storage unit that stores a predictive transfer time which is a predictive time needed to transfer the image data from the receiving device to the inspection management apparatus, and a predictive image processing time which is a predictive time needed to perform image processing on the image data and set for each type of image processing; an input unit that receives input of a scheduled start date and time of the examination and a scheduled start date and time of observation; an image processing unit that performs image processing on the image data; a schedule generation unit that, based on the scheduled start date and time of the examination, the scheduled start date and time of observation, the predictive transfer time, and the predictive image processing time, calculates an image transfer start date and time which is a date and time at which transfer of the image data from the receiving device to the inspection management apparatus is started, and calculates an image processing start date and time which is a date and time at which image processing is started on an image corresponding to the image data that the transfer has been started on the image transfer start date and time; and a control unit that starts acquisition of the image data transmitted from the receiving device when the image transfer start date and time comes, and causes, when the image processing start date and time comes, the image processing unit to perform specified image processing on the image data that the transfer has been started on the image transfer start date and time.

An inspection management system according to another aspect of the invention includes: an inspection management apparatus that manages an examination using a capsule endoscope; and a receiving device that receives and stores image data transmitted from the capsule endoscope, and transfers at least a part of the image data to the inspection management apparatus. The inspection management apparatus includes: a storage unit that stores a predictive transfer time which is a predictive time needed to transfer the image data from the receiving device to the inspection management apparatus, and a predictive image processing time which is a predictive time needed to perform image processing on the image data and set for each type of the image processing; an input unit that receives input of a scheduled start date and time of the examination and a scheduled start date and time of observation; an image processing unit that performs image processing on the image data; a schedule generation unit that, based on the scheduled start date and time of the examination, the scheduled start date and time of observation, the predictive transfer time, and the predictive image processing time, calculates an image transfer start date and time which is a date and time at which transfer of the image data from the receiving device to the inspection management apparatus is started, and calculates an image processing start date and time which is a date and time at which image processing is started on an image corresponding to the image data that the transfer has been started on the image transfer start date and time; and a control unit that starts acquisition of the image data transmitted from the receiving device when the image transfer start date and time comes, and causes, when the image processing start date and time comes, the image processing unit to perform specified image processing on the image data that the transfer has been started on the image transfer start date and time.

An inspection management method according to still another aspect of the invention is executed by an inspection management apparatus for managing an examination performed in a capsule endoscopic system including a receiving device that receives image data from a capsule endoscope and stores the image data. The method includes: receiving input of a scheduled start date and time of the examination and a scheduled start date and time of observation; calculating an image transfer start date and time which is a date and time at which transfer of the image data from the receiving device to the inspection management apparatus is started, and calculating an image processing start date and time which is a date and time at which image processing is started on an image corresponding to the image data that the transfer has been started on the image transfer start date and time, based on the scheduled start date and time of the examination, the scheduled start date and time of observation, a predictive transfer time which is a predictive time needed to transfer the image data from the receiving device to the inspection management apparatus and is stored in a storage unit in advance, and a predictive image processing time which is a predictive time needed to perform image processing on the image data and set for each type of image processing and is stored in the storage unit in advance; starting acquisition of the image data transmitted from the receiving device when the image transfer start date and time comes; and performing, when the image processing start date and time comes, specified image processing on the image data that the transfer has been started on the image transfer start date and time.

A non-transitory computer readable recording medium according to still another aspect of the invention is a recording medium on which an executable program is recorded. The program instructs a processor of a computer, which manages an examination performed in a capsule endoscopic system including a receiving device that receives image data from a capsule endoscope and stores the image data, to execute: receiving input of a scheduled start date and time of the examination and a scheduled start date and time of observation; calculating an image transfer start date and time which is a date and time at which transfer of the image data from the receiving device to the computer is started, and calculating an image processing start date and time which is a date and time at which image processing is started on an image corresponding to the image data that the transfer has been started on the image transfer start date and time, based on the scheduled start date and time of the examination, the scheduled start date and time of observation, a predictive transfer time which is a predictive time needed to transfer the image data from the receiving device to the computer and is stored in a storage unit in advance, and a predictive image processing time which is a predictive time needed to perform image processing on the image data and set for each type of image processing and is stored in the storage unit in advance; starting acquisition of the image data transmitted from the receiving device when the image transfer start date and time comes; and performing, when the image processing start date and time comes, specified image processing on the image data that the transfer has been started on the image transfer start date and time.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is an observation purpose table stored in an observation information table storage unit illustrated in FIG. 3;

FIG. 6 is an image transfer necessary time table stored in the observation information table storage unit illustrated in FIG. 3;

FIG. 7 is an image processing necessary time table stored in the observation information table storage unit illustrated in FIG. 3;

FIG. 8 is a table illustrating an example of a measurement value of an image transfer time for each communication system;

FIG. 9 is a table illustrating an example of a statistic of an image transfer necessary time calculated for each day and each period of time;

FIG. 10 is a table illustrating an example of a measurement value of an image processing time for each image processing content;

FIG. 11 is a table illustrating an example of a statistic of an image processing necessary time calculated for each day and each period of time;

FIG. 12 is a flowchart illustrating operation of the inspection management system illustrated in FIG. 1;

FIG. 13 is a diagram illustrating a display example of an observation schedule setting screen displayed on a display device illustrated in FIG. 1;

FIG. 14 is a table illustrating an example of a process schedule stored in the process schedule storage unit illustrated in FIG. 3;

FIG. 18 is a diagram illustrating a display example of an observation schedule setting screen displayed in an inspection management system according to a second embodiment of the present invention;

FIG. 19 is a table illustrating an example of a process schedule generated based on setting information input in the observation schedule setting screen illustrated in FIG. 18;

FIG. 20 is a table illustrating an example of observation schedule information registered in a receiving device according to the second embodiment of the present invention;

FIG. 22 is a schematic diagram illustrating an example of an observation schedule setting screen displayed on a display device illustrated in FIG. 21;

DETAILED DESCRIPTION OF THE PREFERRED EMBODIMENTS

Exemplary embodiments of an inspection management apparatus, an inspection management system, an inspection management method, and a computer readable recording medium according to the present invention will be described below with reference to the drawings. The present invention is not limited by the embodiments below. Furthermore, in describing the drawings, the same components are denoted by the same reference signs.

First Embodiment

Figure 1:
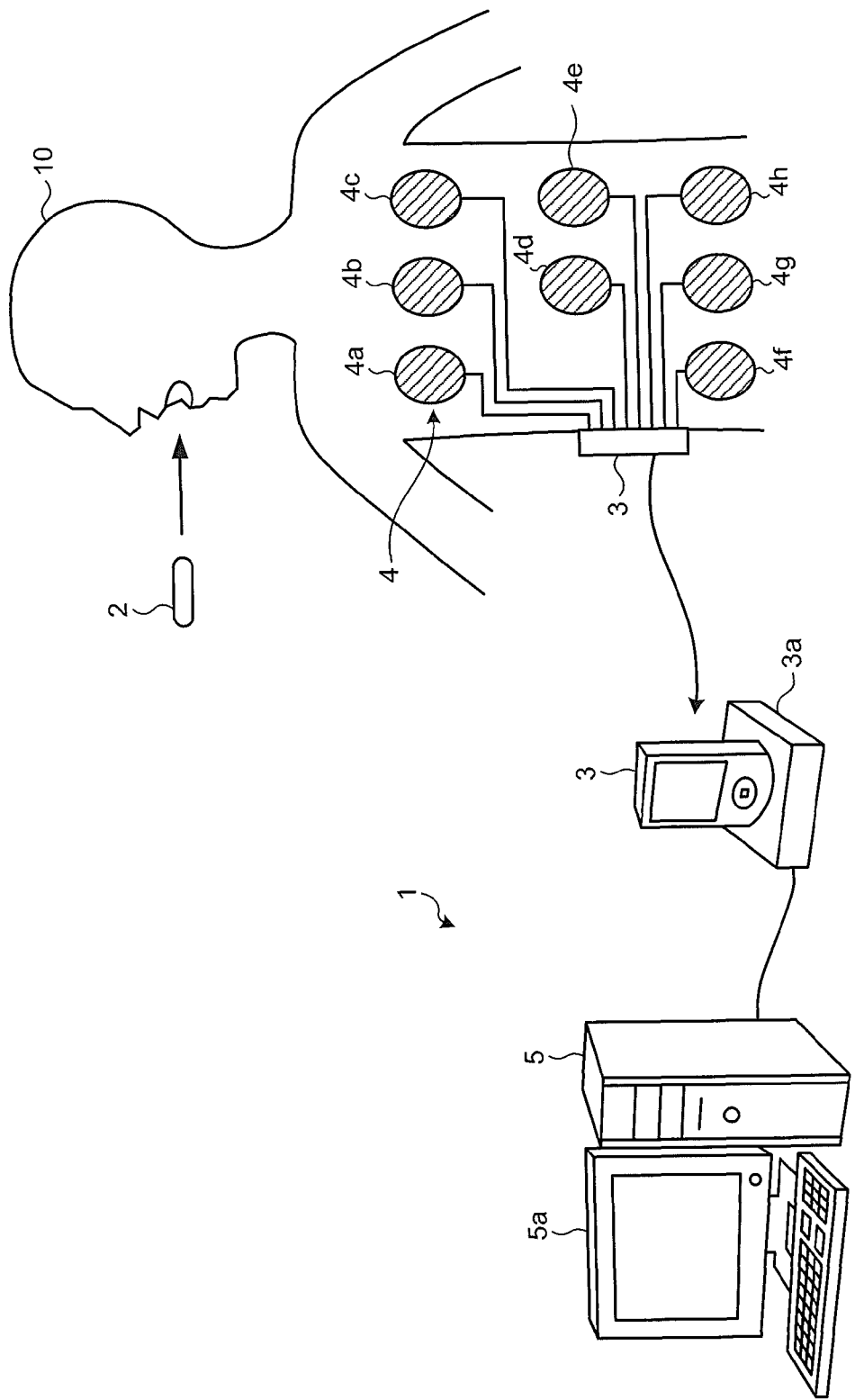
FIG. 1 is a schematic diagram illustrating a schematic configuration of a capsule endoscopic system including an inspection management system according to a first embodiment of the present invention.

FIG. 1 is a schematic diagram illustrating a schematic configuration of a capsule endoscopic system including an inspection management system according to a first embodiment of the present invention. The capsule endoscopic system illustrated in FIG. 1 includes: a capsule endoscope 2 that is introduced into a subject 10 and captures an image of inside of the subject 10; a receiving device 3 that receives a wireless signal wirelessly transmitted from the capsule endoscope 2 introduced in the subject 10 via a receiving antenna unit 4 attached to the subject 10; and an inspection management apparatus 5 that manages examinations using the capsule endoscope 2. Among these devices, the receiving device 3 and the inspection management apparatus 5 form an inspection management system 1 according to the first embodiment.

Figure 2:
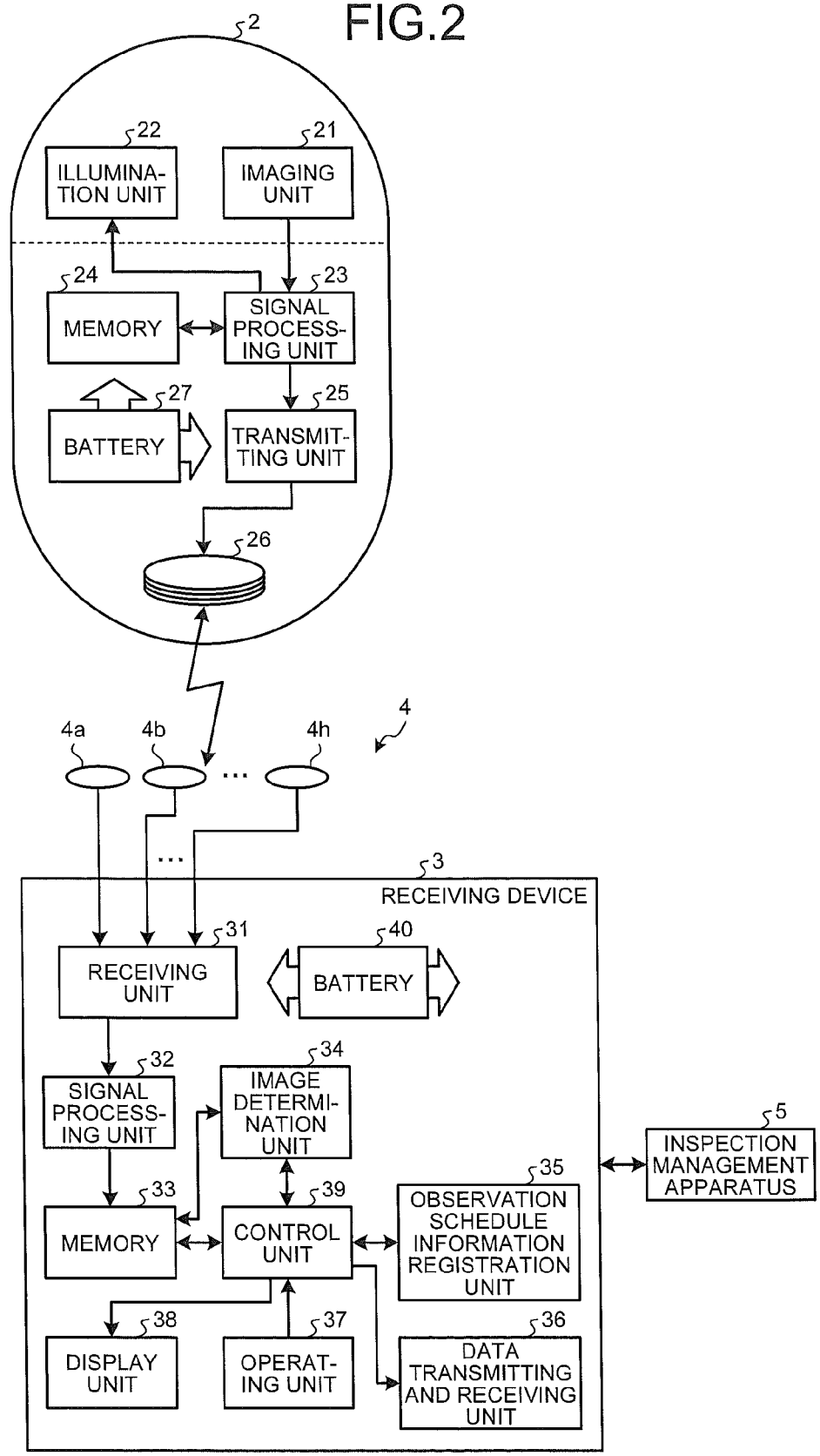
FIG. 2 is a diagram illustrating schematic configurations of a capsule endoscope and a receiving device illustrated in FIG. 1.

FIG. 2 is a block diagram illustrating internal configurations of the capsule endoscope 2 and the receiving device 3. The capsule endoscope 2 is a device that has various built-in parts, such as an imaging element, in a capsule shaped casing of a size swallowable by the subject 10, and includes, as illustrated in FIG. 2: an imaging unit 21 that captures an image of the inside of the subject 10; an illumination unit 22 that illuminates the inside of the subject 10 when an image is captured; a signal processing unit 23; a memory 24; a transmitting unit 25 and an antenna 26; and a battery 27.

The imaging unit 21 includes, for example: an imaging element, such as a CCD or a CMOS, that generates image data of an image representing the inside of the subject 10 based on an optical image formed on a light receiving surface; and an optical system, such as an objective lens, that is arranged on a light receiving surface side of the imaging element.

The illumination unit 22 is realized by a light emitting diode (LED) or the like that emits light toward the inside of the subject 10 when an image is captured. The capsule endoscope 2 has a built-in circuit board (not illustrated) in which a driving circuit or the like that drives each of the imaging unit 21 and the illumination unit 22 is formed. The imaging unit 21 and the illumination unit 22 are fixed on the circuit board such that respective fields of view are directed outward from one end portion of the capsule endoscope 2.

The signal processing unit 23 controls each unit in the capsule endoscope 2, performs A/D conversion on an imaging signal output from the imaging unit 21 to generate digital image data, and further performs specified signal processing on the digital image data.

The memory 24 temporarily stores therein various operation executed by the signal processing unit 23 and the image data subjected to the signal processing in the signal processing unit 23.

The transmitting unit 25 and the antenna 26 superimpose, together with related information, the image data stored in the memory 24 on the wireless signal and transmits the superimposed signal to outside.

The battery 27 supplies electric power to each unit in the capsule endoscope 2. The battery 27 includes a power supply circuit that performs boosting or the like of electric power supplied from a primary battery or secondary battery, such as a button battery.

After being swallowed by the subject 10, the capsule endoscope 2 sequentially captures images of living body sites (an esophagus, a stomach, a small intestine, a large intestine, and the like) at specified time intervals (for example, 0.5 second time interval) while moving inside the digestive tract of the subject 10 by peristaltic movement or the like of organs. The image data and related information generated from acquired imaging signals are sequentially transmitted by wireless to the receiving device 3. The related information includes identification information (for example, a serial number) or the like assigned in order to individually identify the capsule endoscope 2.

The receiving device 3 receives the image data and the related information wirelessly transmitted from the capsule endoscope 2 via the receiving antenna unit 4 including a plurality of receiving antennas 4a to 4h (eight receiving antennas in FIG. 1). Each of the receiving antennas 4a to 4h is realized by using a loop antenna for example, and arranged at a specified position (for example, a position corresponding to one of organs as a passage route of the capsule endoscope 2 in the subject 10) on an outside surface of a body of the subject 10.

As illustrated in FIG. 2, the receiving device 3 includes a receiving unit 31, a signal processing unit 32, a memory 33, an image determination unit 34, an observation schedule information registration unit 35, a data transmitting and receiving unit 36, an operating unit 37, a display unit 38, a control unit 39, and a battery 40.

The receiving unit 31 receives the image data wirelessly transmitted from the capsule endoscope 2 via the receiving antennas 4a to 4h.

The signal processing unit 32 performs specified signal processing on the image data received by the receiving unit 31.

The memory 33 stores therein the image data subjected to the signal processing by the signal processing unit 32 and related information.

The image determination unit 34 determines, from the image data stored in the memory 33, a type of organ (an esophagus, a stomach, a small intestine, a large intestine, or the like) appearing in an image corresponding to the image data, and sets a corresponding image as an object to be transferred. The types of organs are determined by, for example, image color feature data (for example, an average color) calculated through the image processing. Specifically, an average color of an image in which an esophagus appears is whitish to pinkish, an average color of an image in which a stomach appears is reddish, an average color of an image in which a small intestine appears is reddish to yellowish, and an average color of an image in which a large intestine appears is red-brownish.

Alternatively, the image determination unit 34 may determine the types of organs based on an elapsed time since the subject 10 has swallowed the capsule endoscope 2. A segment of time for determining the type of organ may statistically be calculated from an image acquired by a capsule endoscopic examination performed in the past.

Furthermore, the image determination unit 34 may determine an image to be transferred, based on a period of time in which the image is captured by the capsule endoscope 2 (an elapsed time since a specified reference time). Alternatively, an image to be transferred may be determined based on the number of captured images (the order of image capture) obtained by the capsule endoscope 2. If the imaging frame rate (images per second) in the capsule endoscope 2 is constant, the number of captured images corresponds to a period of time in which the images are captured.

The observation schedule information registration unit 35 receives observation schedule information transmitted from the inspection management apparatus 5. The observation schedule information contains information on an image transfer start date and time, which is a date and time at which the receiving device 3 starts to transfer image data to the inspection management apparatus 5, and on an image to be transferred (target image). The observation schedule information may be registered by being directly input by a user using the operating unit 37.

The data transmitting and receiving unit 36 is an interface connectable to a USB or a communication line such as a wired LAN, a wireless LAN, a mobile phone line, Bluetooth (registered trademark) or infrared communication, transmits the image data and the related information stored in the memory 33 to the inspection management apparatus 5, and receives various information transmitted by the inspection management apparatus 5 under control of the control unit 39.

The operating unit 37 is used when a user inputs various types of operation instruction information and setting information in the receiving device 3.

The display unit 38 displays various types of information of which the user is notified.

The control unit 39 controls operation of each unit in the receiving device 3.

The battery 40 supplies electric power to each unit in the receiving device 3.

The receiving device 3 is attached to and carried by the subject 10 while the capsule endoscope 2 is capturing images (for example, while the capsule endoscope 2 passing through the digestive tract after the capsule endoscope 2 is swallowed by the subject 10 and until the capsule endoscope 2 is excreted). During this period, the receiving device 3 adds, to the image data received via the receiving antenna unit 4, related information such as receiving intensity information and receiving time information in each of the receiving antennas 4a to 4h, and stores the image data and the related information in the memory 33. After the capsule endoscope 2 completes the image capturing, the receiving device 3 is removed from the subject 10, is then connected to the inspection management apparatus 5, and transfers the image data stored in the memory 33 to the inspection management apparatus 5. In FIG. 1, a cradle 3a is connected to a USB port of the inspection management apparatus 5, and by setting the receiving device 3 in the cradle 3a, the receiving device 3 is connected to the inspection management apparatus 5. Furthermore, while the capsule endoscope 2 is capturing images, the receiving device 3 transmits, on a designated date and time, a target image designated in the observation schedule information to the inspection management apparatus 5 via an available communication line or the like.

The inspection management apparatus 5 is configured by using, for example, a workstation including a display device 5a, such as a CRT display or a liquid crystal display. The inspection management apparatus 5 generates a series of schedules of examinations using the capsule endoscope 2 based on the information input by the user, manages the examinations, performs specified image processing on images of the inside of the subject 10 that are acquired via the receiving device 3, and displays the processed images on the display device 5a.

In general, an examination using the capsule endoscope 2 is performed according to the following procedure: the capsule endoscope 2 is swallowed by the subject 10; the capsule endoscope 2 transmits image data generated by capturing images of the inside of the subject 10 to the receiving device 3; the image data accumulated in the receiving device 3 are transferred to the inspection management apparatus 5 after completion of the image capturing by the capsule endoscope 2; and the inspection management apparatus 5 performs specified image processing on the acquired image data to generate images for observation.

In contrast, the inspection management apparatus 5 according to the first embodiment generates a schedule so that a process (transfer of image data and image processing) to be performed on images according to the observation purpose of a user, such as a medical worker, can be completed by an observation scheduled date and time in order to enable the user to observe desired images at a desired timing. In the present specification, the observation purpose is an item as a combination of a region to be observed (an esophagus, a stomach, a small intestine, a large intestine, the entirety, or the like), an observation method (lesion image observation, representative image observation, entire image observation), and the like. Details of the observation purpose will be described later.

Figure 4:
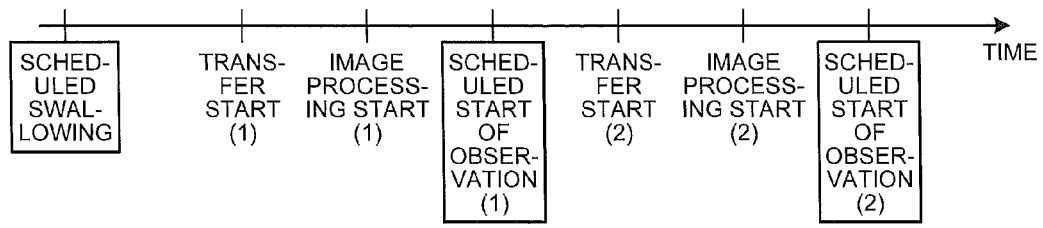
FIG. 4 is a diagram illustrating an outline of a process schedule generated by the inspection management system illustrated in FIG. 1.

FIG. 4 is a diagram illustrating an outline of the above described process schedule. Of all schedules illustrated in FIG. 4, a scheduled swallowing date and time at which the capsule endoscope 2 is swallowed by the subject 10 and a scheduled start date and time of observation at which a medical worker starts observation are input by a user. In contrast, a transfer start date and time at which the receiving device 3 starts to transfer image data to the inspection management apparatus 5 and an image processing start date and time at which image processing is started in the inspection management apparatus 5 are automatically calculated by the inspection management apparatus 5 based on the scheduled swallowing date and time and the scheduled start date and time of observation. Furthermore, the transfer of image data and the image processing may be divided and performed in parts depending on the observation purpose. In FIG. 4, two sets of transfer starts (1) and (2) and image processing starts (1) and (2) corresponding to two respective scheduled observation starts (1) and (2) are illustrated.

Figure 3:
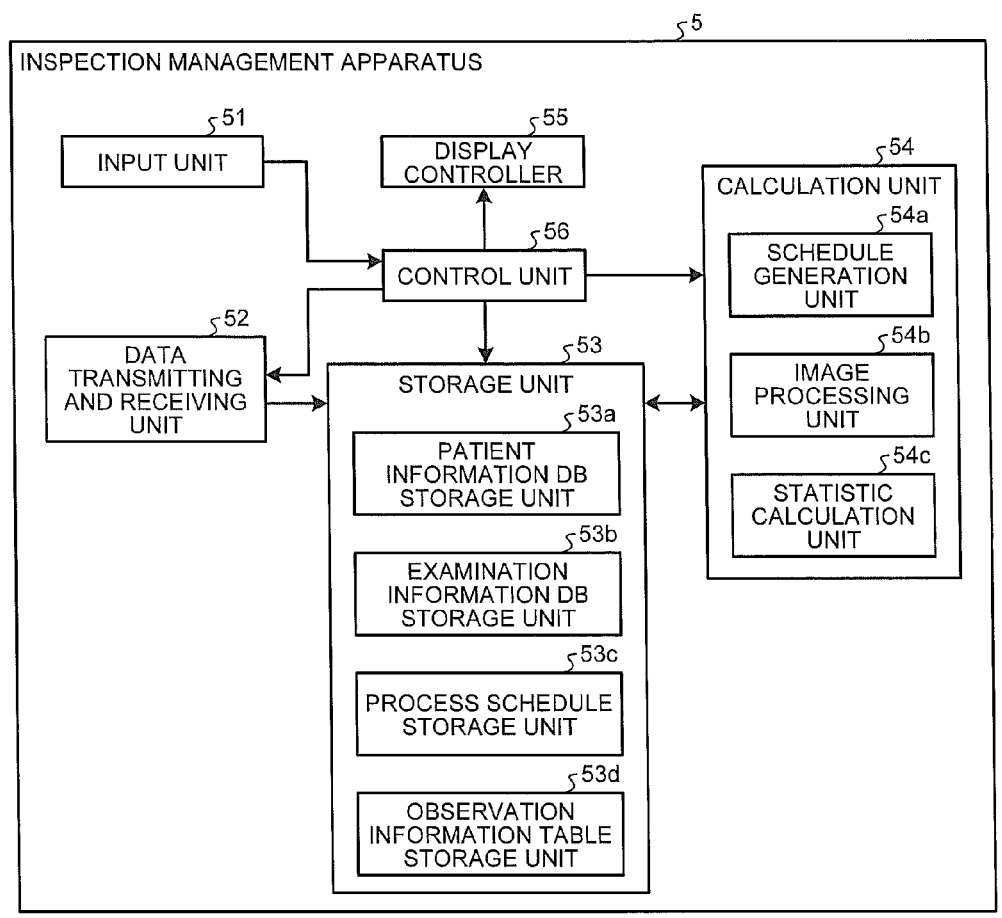
FIG. 3 is a block diagram illustrating a schematic configuration of an inspection management apparatus illustrated in FIG. 1.

As illustrated in FIG. 3, the inspection management apparatus 5 includes an input unit 51, a data transmitting and receiving unit 52, a storage unit 53, a calculation unit 54, a display controller 55, and a control unit 56.

The input unit 51 is realized by an input device, such as a keyboard, a mouse, a touch panel, or various switches. The input unit 51 receives input of information and an instruction according to user's operation.

The data transmitting and receiving unit 52 is an interface connectable to a USB or a communication line, such as a wired LAN, a wireless LAN, a mobile phone line, infrared, or Bluetooth (registered trademark), and includes a USB port, a LAN port, or the like. The data transmitting and receiving unit 52 functions as a data acquisition unit that acquires the image data and the related information from the receiving device 3 via an external device, such as the cradle 3a, or various communication lines connected to the USB port, and functions as a transmitting unit that transmits various information including the observation schedule information to the receiving device 3.

The storage unit 53 is realized by a semiconductor memory such as a flash memory, a RAM, a ROM, or a recording medium such as an HDD, an MO, a CD-R, or a DVD-R, and a read and write device or the like that reads and writes information from and to the recording medium. The storage unit 53 stores therein programs and various information for causing the inspection management apparatus 5 to operate and execute various functions, image data acquired from the receiving device 3, and various information for managing examinations using the capsule endoscope 2. More specifically, the storage unit 53 includes a patient information database (DB) storage unit 53a, an examination information database storage unit 53b, a process schedule storage unit 53c, and an observation information table storage unit 53d.

The patient information database storage unit 53a stores therein a database containing information, as information on a patient that is the subject 10, information including a patient ID, a name, a date of birth, sex, a disease and injury name, and the like.

The examination information database storage unit 53b stores therein a database containing, as information on an examination using the capsule endoscope 2, information including an examination ID (examination identification code), a patient ID (a patient identification code) of a patient who is to have the examination, an examination date and time, an organ to be observed, and the like.

The process schedule storage unit 53c stores therein the process schedule generated as described above by the inspection management apparatus 5. Details of the process schedule will be described later.

The observation information table storage unit 53d stores therein various observation information tables that are referred to when the process schedule is generated. FIG. 5 to FIG. 7 illustrate examples of the observation information tables stored in the observation information table storage unit 53d.

FIG. 5 is an observation purpose table, in which a type of the observation purpose, an image (target image) to be observed according to the observation purpose, and a type of image processing to be performed on the image according to the observation purpose are associated with one another. In the observation purpose table illustrated in FIG. 5, each observation purpose is managed by a type code.

"Lesion image observation" indicated by a type code 001 is an observation method of observing a lesion image extracted by image processing to recognize presence or absence of a lesion, and all of images captured by the capsule endoscope 2 are employed as target images. The "lesion image observation" is associated with a lesion detection process as image processing. The lesion detection process is executed every time the inspection management apparatus 5 acquires an image, or is executed collectively after all of images to be observed are acquired.

"Lesion image observation" for an individual organ (an esophagus, a stomach, a small intestine, or a large intestine) indicated by each of type codes 005 to 008 employs an individual organ selected by a user as a target image with respect to the above described "lesion image observation". The "lesion image observation" for an individual organ is associated with an organ discrimination process, together with the above described lesion detection process. The organ discrimination process and the lesion detection process are executed every time the inspection management apparatus 5 acquires an image, or are executed collectively after all of images to be observed are acquired.

The "lesion image observation" using all of the images or images of a selected individual organ may be performed by a medical worker in a spare time before or after work or before or after a break.

"Representative image observation" indicated by a type code 002 is an observation method of observing a representative image extracted by image processing to grasp the overview of a series of images captured by the capsule endoscope 2, and all of images are employed as target images. The "representative image observation" is associated with a representative image extraction process as image processing. The representative image extraction process is executed when the inspection management apparatus 5 acquires all of images captured by the capsule endoscope 2.

"Representative image observation" for an individual organ indicated by each of type codes 009 to 012 employs an individual organ selected by a user as a target image with respect to the above described "representative image observation". The "representative image observation" for an individual organ is associated with an organ discrimination process, together with the above described representative image extraction process. The organ discrimination process and the representative image extraction process are executed when all of images of a target organ are acquired.

The "representative image observation" using all of the images or images of a selected individual organ may be performed after all of the images are captured or in a spare time after images of a target organ are captured.

"Entire image observation" indicated by a type code 003 is an observation method of observing all of images captured by the capsule endoscope 2 to confirm whether a lesion is not overlooked for example. The "entire image observation" is associated with a similar image detection process, a red detection process, and a position detection process as image processing. These image processing processes are executed when all of the images are acquired.

"Entire image observation" for an individual organ indicated by each of type codes 013 to 016 is associated with an organ discrimination process and the similar image detection process. These image processing processes are executed when all of images of a target organ are acquired.

The "entire image observation" using all of the images or images of a selected individual organ may be performed when an adequate time is available, for example, at the end of everyday work.

FIG. 6 is an image transfer necessary time table indicating statistics of a time needed to transfer a single image (hereinafter, referred to as an image transfer necessary time) according to a communication method used when image data is transferred from the receiving device 3 to the inspection management apparatus 5. Specifically, an average value, a maximum value, a minimum value, a mode value, and a median value of an image transfer necessary time calculated based on examinations performed in the past by the inspection management apparatus 5 are recorded for each communication system, such as a USB, a wireless LAN, a mobile phone line, and integration. Of the communication systems, the integration indicates values calculated from an image transfer necessary time needed to transfer all of images without discriminating the communication systems.

FIG. 7 is an image processing necessary time table indicating statistics of a time needed to perform image processing on a single image (hereinafter, referred to as an image processing necessary time) according to a type of image processing performed by the inspection management apparatus 5. Specifically, an average value, a maximum value, a minimum value, a mode value, and a median value of an image processing time calculated based on examinations performed in the past by the inspection management apparatus 5 are recorded for each image processing, such as the lesion detection process, a representative image detection process, the similar image detection process, the red detection process, the position detection process, and an organ detection process.

Referring back to FIG. 3, the calculation unit 54 is realized by hardware, such as a CPU, and by reading an image display program, manages the examinations using the capsule endoscope 2 based on information input via the input unit 51, performs specified image processing on image data acquired via the data transmitting and receiving unit 52, and generates image data to display an image in a specified format.

More specifically, the calculation unit 54 includes a schedule generation unit 54*a*, an image processing unit 54*b*, and a statistic calculation unit 54*c*. The schedule generation unit 54*a* calculates an image transfer start date and time and an image processing start date and time and generates a process schedule by referring to the observation information tables illustrated in FIGS. 5 to 7 based on the scheduled swallowing date and time, the scheduled start date and time of observation, and the observation purpose input by a user.

The image processing unit 54*b* performs common image processing, such as a white balance process, demosaicing, color conversion, density conversion (gamma conversion or the like), smoothing (noise elimination or the like), or sharpening (edge enhancement or the like), on the image data that is transferred from the receiving device 3 and stored in the storage unit 53, and performs image processing, such as the lesion detection process, the representative image detection process, the similar image detection process, the red detection process, the position detection process, or the organ detection process, on an image of a designated area according to the observation purpose.

The statistic calculation unit 54*c* calculates a statistic of each of the image transfer necessary time and the image processing necessary time based on examinations performed by the inspection management apparatus 5 in a past specified period or in the entire period, and generates tables as illustrated in FIG. 6 and FIG. 7.

For example, as illustrated in FIG. 8, the statistic calculation unit 54*c* acquires and accumulates a communication method (a USB, a wireless LAN, a mobile phone line, or the like), the number of transferred images, and a measurement time of a time needed to transfer the images (an image transfer time) for each examination identification code, and calculates an average value, a maximum value, a minimum value, a mode value, and a median value of the image transfer necessary time as illustrated in FIG. 6 based on the accumulated information.

An image data transfer speed greatly changes depending on the amount of communication due to other processes being performed in parallel, for example, depending on the state of a process of backing up data to an HIS (Hospital Information System), an RIS (Radiology Information System), a PACS (Picture Archiving and Communication Systems), a NAS (Network Attached Storage), or the like. Therefore, the statistic calculation unit 54*c* may process the information accumulated with respect to transfer of image data for each day or each period of time for example, and may calculate the statistics of the image transfer necessary time for each day or each period of time (see, for example, FIG. 9).

Furthermore, as illustrated in FIG. 10, the statistic calculation unit 54*c* acquires and accumulates a type of image processing, the number of images subjected to the image processing (the number of target images), and a measurement value of a time needed to perform the image processing on the images (a processing time) for each examination identification code, and calculates an average value, a maximum value, a minimum value, a mode value, and a median value of the image processing necessary time as illustrated in FIG. 7 based on the accumulated information.

An image processing speed greatly changes depending on loads on the CPU or the usage of the memory due to other processes being performed in parallel. Therefore, the statistic calculation unit 54*c* may process the information accumulated with respect to image processing for each day or each period of time for example, and may calculate the statistics of the image processing necessary time for each day or each period of time (see, for example, FIG. 11).

The display controller 55 causes the display device 5*a* to display a specified screen under control of the control unit 56. Specifically, the display controller 55 displays, on the display device 5*a*, a screen that allows a user to input various information when a schedule of a capsule endoscopic examination is to be generated, or an observation screen including an image subjected to image processing by the image processing unit 54*b*.

The control unit 56 is realized by hardware, such as a CPU, and by reading various programs stored in the storage unit 53, transfers instructions or data to each unit of the inspection management apparatus 5 based on signals input via the input unit 51, image data acquired via the data transmitting and receiving unit 52, or the like, and integrally controls the entire operation of the inspection management apparatus 5.

As a specific process, for example, the control unit 56 causes the data transmitting and receiving unit 52 to transmit the image transfer start date and time calculated by the schedule generation unit 54a to the receiving device 3 and to fetch image data transmitted from the receiving device 3 when the image transfer start date and time comes. Furthermore, when the image processing start date and time calculated by the schedule generation unit 54a comes, the control unit 56 causes the image processing unit 54b to perform specified image processing on an image corresponding to the image data started to be transferred on the image transfer start date and time.

Next, operation of the inspection management system 1 will be described. FIG. 12 is a flowchart illustrating the operation of the inspection management system 1.

A user makes an appointment for an examination in the inspection management apparatus 5. Specifically, the user inputs examination information and patient information in the inspection management apparatus 5 to establish an examination workflow.

In response to this, at Step S10, the inspection management apparatus 5 displays, on the display device 5a, an observation schedule setting screen that allows a user to input an observation schedule. FIG. 13 illustrates a display example of the observation schedule setting screen. An observation schedule setting screen M1 illustrated in FIG. 13 contains a display field m11 for an observation schedule identification number (hereinafter, this may be simply described as a number), a display field m12 for a patient name of the subject 10, an entry field m13 for a scheduled swallowing date and time, an entry field m14 for a scheduled start date and time of observation, a display and selection field m15 for an observation purpose, and an entry field m16 for a doctor name. Of these fields, the display and selection field m15 for an observation purpose allows a user to select a desired observation purpose from among a plurality of observation purposes displayed in a drop-down list. In the observation schedule setting screen M1, the entry fields (the number of lines) can be increased by user's operation.

The user inputs, in the observation schedule setting screen M1, a scheduled swallowing date and time at which the capsule endoscope 2 is swallowed, one or more combinations of a scheduled start date and time of observation and an observation purpose, and a doctor name for a single examination (a single patient). In this case, it is preferable to input the scheduled start date and time of observation by taking into account a doctor's work schedule for a day. In FIG. 13, four combinations of the scheduled start date and time of observation and the observation purpose are input for a patient name ZZZ, and two combinations of the scheduled start date and time of observation and the observation purpose are input for a patient name YYY.

At Step S11, the inspection management apparatus 5 receives input of setting information including the scheduled start date and time of observation and the observation purpose, and stores the setting information in the process schedule storage unit 53c. FIG. 14 is a table illustrating an example of a process schedule stored in the process schedule storage unit 53c. A process schedule M2 illustrated in FIG. 14 contains a recording field m21 for a scheduled swallowing date and time, a recording field m22 for a scheduled start date and time of observation, and a recording field m23 for an observation purpose, which are recorded based on the setting information input by the user. The process schedule M2 further contains a recording field m24 for the number of images for time calculation, which is used to calculate an image data transfer time and an image processing time, a recording field m25 for an average value of the image processing necessary time, a recording field m26 for an image processing time, a recording field m27 for an image processing start date and time, a recording field m28 for an average value of the image transfer necessary time, a recording field m29 for an image transfer time, and a recording field m30 for an image transfer start date and time.

At subsequent Step S12, the inspection management apparatus 5 generates a process schedule based on the received setting information. More specifically, the schedule generation unit 54a performs calculations according to procedures (i) to (vi) below by referring to the observation information tables illustrated in FIG. 5 to FIG. 7 based on the scheduled start date and time of observation and the observation purpose, and calculates the image transfer start date and time and the image processing start date and time for each observation purpose.

(i) A number-of-images calculation time to be a basis for a calculation of the number of images is calculated according to Equations (1) and (2) below based on the scheduled swallowing date and time, the scheduled start date and time of observation, and a previous image transfer start date and time. If the initial (first) scheduled start date and time of observation is to be calculated, the previous image transfer start date and time corresponds to the scheduled swallowing date and time.

First time:

(Number-of-images calculation time)=(Scheduled start date and time of observation)−(Scheduled swallowing date and time) (1)

For example, in the case with the observation schedule identification number of 1 in FIG. 13, the scheduled start date and time of observation is Feb. 3, 2012, 11:15, and the scheduled swallowing date and time is Feb. 3, 2012, 10:15; therefore, the number-of-images calculation time becomes 6000 seconds.

Second or later time:

(Number-of-images calculation time)=(Scheduled start date and time of observation)−(Previous image transfer start date and time) (2)

For example, in the case with the observation schedule identification number of 2 in FIG. 13, the scheduled start date and time of observation is Feb. 3, 2012, 14:25, and the previous image transfer start date and time (for the observation schedule identification number of 1) is Feb. 3, 2012, 11:48 as will be described later; therefore, the number-of-images calculation time becomes 157 minutes (=9420 seconds).

(ii) The number of images for time calculation is calculated according to Equation (3) below based on the number-of-images calculation time and the number of images captured by the capsule endoscope per second.

(Number of images for time calculation)=(Number-of-images calculation time)×(Number of images captured per second) (3)

For example, in the case with the observation schedule identification number of 1 in FIG. 13, the number-of-images calculation time is 6000 seconds; therefore, if the imaging frame rate of the capsule endoscope 2 is two images per second, the number of images for time calculation becomes 12000. The calculated number of images for time calculation is recorded in the recording field m24 illustrated in FIG. 14.

(iii) A time needed for image processing (an image processing time) is calculated according to Equation (4) below based on the number of images for time calculation and a predictive value of the image processing necessary time. As the predictive value of the image processing necessary time, a statistic illustrated in FIG. 7 is used.

(Image processing time)=(Number of images for time calculation)×(Predictive value of image processing necessary time)     (4)

For example, in the case with the observation schedule identification number of 1 in FIG. 13, the observation purpose is to observe a lesion image of an esophagus; therefore, with reference to FIG. 5, necessary image processing is the organ discrimination process and the lesion detection process. Furthermore, average values of the image processing necessary times for the organ discrimination process and the lesion detection process are 0.020 (seconds per image) and 0.010 (seconds per image), respectively, so that the total becomes 0.030 seconds (see the recording field m25). Moreover, because the number of images for time calculation is 12000 images as described above, the image processing time becomes 12000 images×0.030 (seconds per image)=360 seconds (=6 minutes). The calculated image processing time is recorded in the recording field m26.

As the statistic of the image processing necessary time, a value other than the average value may be used. It may be possible to allow a user to appropriately select any of the average value, the maximum value, the minimum value, the mode value, and the median value to be used, or may cause the inspection management apparatus 5 to automatically select any of them. Alternatively, test results or the like obtained in the development of the inspection management apparatus 5 may be set in advance as initial values in the inspection management apparatus 5.

(iv) An image processing start date and time is calculated according to Equation (5) below based on the scheduled start date and time of observation and the image processing time.

(Image processing start date and time)=(Scheduled start date and time of observation)−(Image processing time)     (5)

For example, in the case with the observation schedule identification number of 1 in FIG. 13, the scheduled start date and time of observation is Feb. 3, 2012, 11:15 and the image processing time is 6 minutes; therefore, the image processing start date and time becomes Feb. 3, 2012, 11:49. The calculated image processing start date and time is recorded in the recording field m27.

(v) An image transfer time is calculated according to Equation (6) below based on the number of images for time calculation and the predictive value of the image transfer necessary time. As the predictive value of the image transfer necessary time, the statistic illustrated in FIG. 6 is used.

(Image transfer time)=(Number of images for time calculation)×(Predictive value of image transfer necessary time)     (6)

For example, when image data is to be transferred by a wireless LAN, the image transfer necessary time is 0.0050 (seconds per image) (see the recording field m28). Furthermore, the number of images for time calculation is 12000 images as described above. Therefore, the image transfer time becomes 12000 images×0.0050 (seconds per image)=60 seconds (=1 minute). The calculated image transfer time is recorded in the recording field m29.

The communication line used for the image data may be set in advance by a user. Alternatively, the inspection management apparatus 5 may select an available communication line at the time, or the communication line may be determined in advance as specifications. Furthermore, as the statistic of the image transfer necessary time, a value other than the average value may be used. It may be possible to allow a user to appropriately select any of the average value, the maximum value, the minimum value, the mode value, and the median value to be used or may cause the inspection management apparatus 5 to automatically select any of them. Alternatively, test results or the like obtained in the development of the inspection management apparatus 5 may be set in advance as initial values in the inspection management apparatus 5.

(vi) An image transfer start date and time is calculated according to Equation (7) below based on the image processing start date and time and the image transfer time.

(Image transfer start date and time)=(Image processing start date and time)−(Image transfer time)     (7)

For example, in the case with the observation schedule identification number of 1 in FIG. 13, the image processing start date and time is Feb. 3, 2012, 11:49 and the image transfer time is 1 minute; therefore, the image transfer start date and time becomes Feb. 3, 2012, 11:48. The calculated date and time is recorded in the recording field m30.

The image processing start date and time (for example, Feb. 3, 2012, 11:49) and the image transfer start date and time (11:48 on the same date) calculated as described above are recorded in the process schedule.

Figure 15:
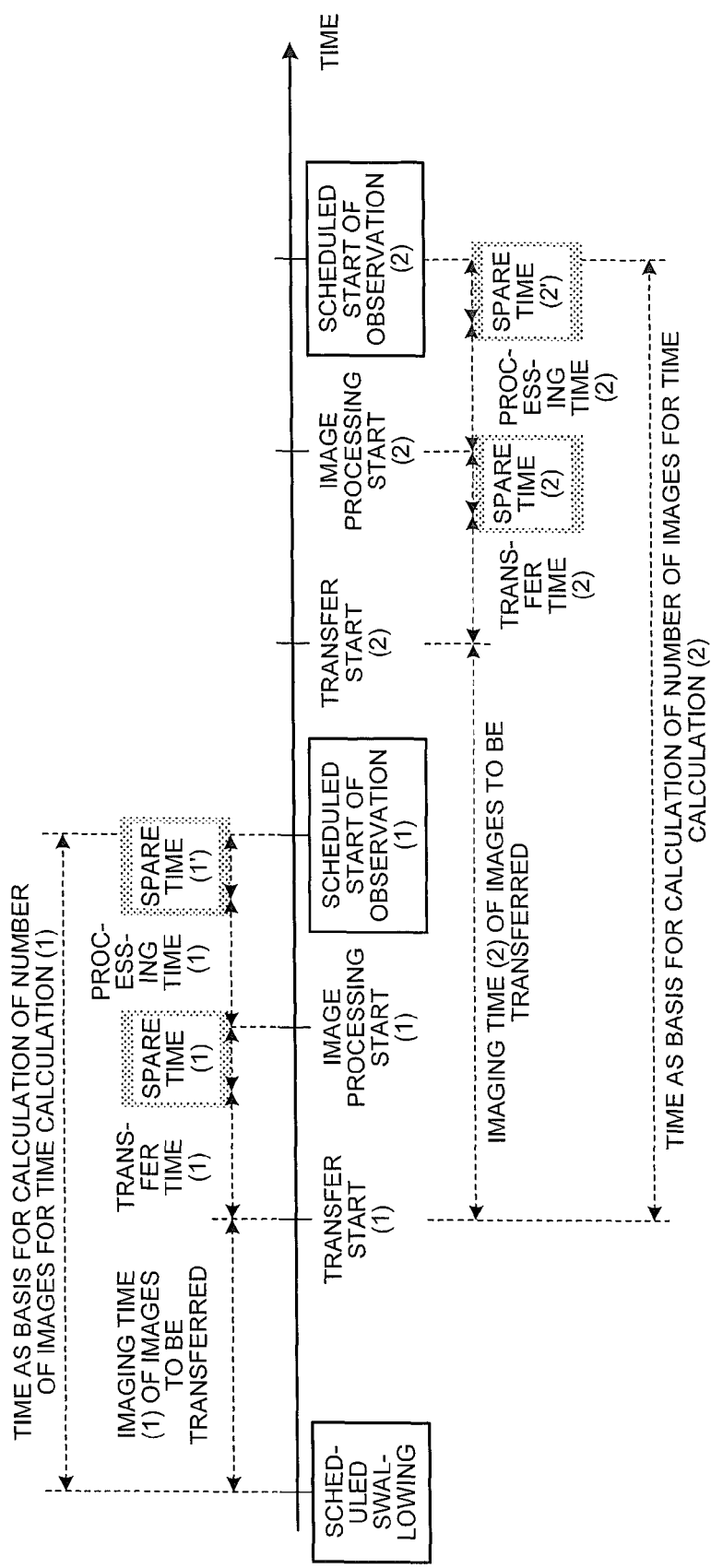
FIG. 15 is a diagram illustrating spare times in the flow of a series of examinations performed in the inspection management system illustrated in FIG. 1.

In the procedure (i), times used as bases for calculating the number of images for time calculation (1) and the number of images for time calculation (2) are set to a time from scheduled swallowing to a scheduled observation start (1) and a time from a transfer start (1) to a scheduled observation start (2), respectively (see FIG. 15). In contrast, images to be actually transferred are captured before the transfer starts (1) and (2) (the image capturing times (1) and (2) of the image to be transferred). Therefore, when an examination is actually started, as illustrated in FIG. 15, spare times (spare times (1), (1'), (2), and (2')) occur between the end of image transfer and the start of image processing, or between the end of image processing to the start of an observation.

At subsequent Step S13, the inspection management apparatus 5 initializes the receiving device 3 and registers the observation schedule information. More specifically, when the receiving device 3 is connected to the inspection management apparatus 5 via the cradle 3a, the inspection management apparatus 5 deletes the examination information, the patient information, the observation schedule information, and the image data on past examinations stored in the receiving device 3, and newly registers the examination information, the patient information, and the observation schedule information on an examination to be performed next. In this case, it may be possible to additionally register identification information (a computer name, an IP address, or the like) on the inspection management apparatus 5.

Figures 16, 17:
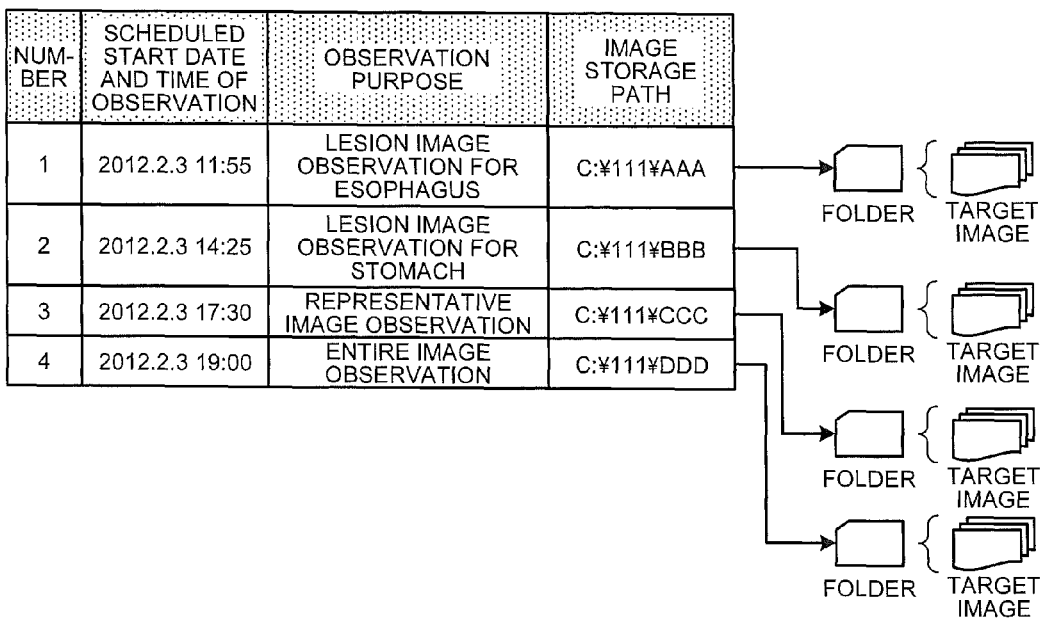
FIG. 16 is a table illustrating an example of observation schedule information registered in the receiving device illustrated in FIG. 1.
FIG. 17 is a diagram illustrating an example of designation of an image storage path in the inspection management apparatus illustrated in FIG. 1.

FIG. 16 is a table illustrating an example of the observation schedule information registered in the receiving device 3. As illustrated in FIG. 16, the observation schedule information contains information on a transfer target image and an image transfer start date and time, which are set in accordance with an observation purpose for the subject 10 (for example, the patient name ZZZ illustrated in FIG. 13) to which the receiving device 3 is attached.

The examination information, the patient information, and the observation schedule information may be registered in the receiving device 3 by the user by directly inputting the information from the operating unit 37 of the receiving device 3.

Thereafter, the user explains the examination to the subject 10 and attaches the receiving antenna unit 4 to the subject 10, and when the scheduled swallowing date and time comes, the subject 10 swallows the capsule endoscope 2. Accordingly, the examination is started (Step S14), and the capsule endoscope 2 captures images while moving inside the subject 10 and sequentially transmits generated image data wirelessly to the receiving device 3. In response to this, the receiving device 3 sequentially stores the received image data in the memory 33. After the capsule endoscope 2 is swallowed and the user confirms that the capsule endoscope 2 has passed through the stomach, the subject 10 is allowed to freely act up to the time designated by the user. Whether the capsule endoscope 2 has passed through the stomach can be determined by the user based on an image displayed on the display unit 38 in a simplified manner based on image data that the receiving device 3 has received from the capsule endoscope 2.

Thereafter, the inspection management system 1 performs a process of a loop A for each observation purpose. That is, at Step S15, the receiving device 3 determines whether the image transfer start date and time has passed. If the image transfer start date and time has not already passed (Step S15: No), the receiving device 3 waits until the image transfer start date and time has passed (Step S16).

In contrast, if the image transfer start date and time has passed (Step S15: Yes), the receiving device 3 determines image data of an image corresponding to the observation purpose from among image data stored in the memory 33, and transfers the determined image data to the inspection management apparatus 5 (Step S17).

More specifically, the receiving device 3 first recognizes a communication system available at this time (a USB or a communication line such as a wired LAN, a wireless LAN, a mobile phone line, infrared, Bluetooth (registered trademark); hereinafter, they may collectively be referred to as a communication line or the like). The available communication system may be set in advance by a user, or may automatically be selected by the receiving device 3 from among communication systems available at this time. Alternatively, it may be possible to use a communication system designated in advance as specifications.

Subsequently, the receiving device 3 sequentially transmits, to the inspection management apparatus 5 via the recognized communication line or the like, image data corresponding to transfer target images (namely, target images for the respective purposes illustrated in FIG. 5) based on the observation schedule information. In this case, if a transfer target image is an "entire image", the receiving device 3 transmits all of the image data accumulated in the memory 33 in the order that the images are captured. Furthermore, if a transfer target image is an image of an individual organ, that is, any of an "esophagus image", a "stomach image", a "small intestine image", and a "large intestine image", the receiving device 3 causes the image determination unit 34 to perform an image determination process on the image data accumulated in the memory 33, and sequentially transmits only image data corresponding to the target organ in the order that the images are captured, in accordance with the determination result obtained by the image determination unit 34.

If image data of the transfer target image has already been transmitted when the image transfer start date and time comes, it is not necessary to transfer the image data. For example, after image data of the "entire image" captured in a certain period has been transferred, if an "esophagus image" in the same period is determined as a transfer target image, it is not necessary to transfer the image data of the esophagus image.

At subsequent Step S18, the inspection management apparatus 5 stores and manages the image data transferred by the receiving device 3 for each observation purpose. For example, as illustrated in FIG. 17, the inspection management apparatus 5 designates an image storage path for each observation purpose, with respect to the image data of the target image acquired from the receiving device 3, and stores the image data of each target image in a designated folder.

At Step S19, the inspection management apparatus 5 determines whether the image processing start date and time has passed. If the image processing start date and time has not already passed (Step S19: No), the inspection management apparatus 5 waits until the image processing start date and time has passed (Step S20).

In contrast, if the image processing start date and time has passed (Step S19: Yes), the inspection management apparatus 5 performs image processing corresponding to the observation purpose on the images stored in the folder corresponding to the observation purpose for which the image processing start date and time has passed (Step S21).

After image data corresponding to all of the set observation purposes are transferred and subjected to image processing, the inspection management apparatus 5 waits until the capsule endoscope 2 completes the examination.

After Step S14, when the scheduled start date and time of observation comes for each observation purpose, the inspection management apparatus 5 may generate an observation screen including images corresponding to the observation purpose and displays the observation screen on the display device 5a according to input of operation by the user via the input unit 51.

When the examination ends at Step S22, the user removes the receiving device 3 from the subject 10 and connects the receiving device 3 to the inspection management apparatus 5 via the cradle 3a. In response to this, at Step S23, the receiving device 3 transfers, to the inspection management apparatus 5, image data that have not been transferred, and the inspection management apparatus 5 performs common image processing, such as a white balance process or demosaicing, on the acquired image data. Thereafter, the image data subjected to the image processing is stored, and the operation by the inspection management system 1 ends.

As described above, according to the first embodiment, image processing corresponding to an observation purpose is performed on an image corresponding to the observation purpose, in accordance with the observation purpose and the scheduled start date and time of observation that are registered in advance. Therefore, a medical worker becomes able to perform necessary observation at a convenient timing according to his/her work schedule. Consequently, the medical worker becomes able to perform observations by effectively using spare times between busy schedules.

Modified Example

In the above described first embodiment, an image to be observed (transfer target) and a type of image processing are automatically set according to an observation purpose. However, it may be possible to allow a user to manually set an image to be observed and a type of image processing. In this case, it is preferable to provide a field for designating an image to be observed and a field for designating a type of image processing, instead of the display and selection field m15 for an observation purpose in the observation schedule setting screen M1 illustrated in FIG. 13 or in addition to the display and selection field m15.

Furthermore, the image to be observed may be designated for each type of organ. For example, an image to be observed may be designated according to a period of time in which the image is captured by the capsule endoscope 2. Specifically, when an image near an esophagus is to be observed for example, the user designates "00:00 to 00:01" as a period of time in which the image is captured, instead of designating an "esophagus" as an object to be observed. In this case, in the receiving device 3, the image determination unit 34 determines images captured before one minute has passed since swallowing of the capsule endoscope 2 as transfer targets, and the data transmitting and receiving unit 36 transfers the images to the inspection management apparatus 5 according to the set scheduled start date and time of observation and the image processing start date and time.

Alternatively, it may be possible to designate an image to be observed based on the order that images are captured by the capsule endoscope 2 (the number of captured images counted from a specified timing), instead of the period of time in which images are captured. For example, when an image near an esophagus is to be observed, "1st to 120th" is designated as the order of image capture. In this case, the image determination unit 34 determines the first to the 120th images captured by the capsule endoscope 2 as transfer targets. The counting of the number of captured images for determining transfer target images may be started at the start of image capturing operation of the capsule endoscope 2 or when the capsule endoscope 2 is swallowed.

Second Embodiment

Next, a second embodiment of the present invention will be described.

In the above described first embodiment, a process schedule is generated based on the observation purpose and the scheduled start date and time of observation input by the user. In contrast, a feature of the second embodiment is that an observation schedule is generated by taking into account a date and time at which the subject 10 revisits a hospital after he/she has swallowed the capsule endoscope 2 and temporarily left the hospital. The configuration and operation of an inspection management system according to the second embodiment are the same as those illustrated in FIG. 1 to FIG. 3 and FIG. 12.

At Step S10 in FIG. 12, the inspection management apparatus 5 displays an observation schedule setting screen on the display device 5a. FIG. 18 is a schematic diagram illustrating an example of the observation schedule setting screen. In an observation schedule setting screen M3 illustrated in FIG. 18, an entry field m31 for a scheduled date and time of patient revisit is provided in addition to the fields in the observation schedule setting screen M1 illustrated in FIG. 13. The entry field m31 for the scheduled date and time of patient revisit is a field for inputting a time, at which the subject 10 as a patient who has swallowed the capsule endoscope 2 and been released temporarily needs to come back to the hospital, and is input together with the scheduled swallowing date and time, the scheduled start date and time of observation, and the observation purpose by the user.

At Step S11, the input unit 51 receives the scheduled date and time of patient revisit input by the user, together with the scheduled start date and time of observation and the observation purpose.

At subsequent Step S12, the schedule generation unit 54a generates a process schedule based on the received setting information, similarly to the first embodiment.

FIG. 19 is a table illustrating an example of the process schedule generated based on the setting information input in the observation schedule setting screen M3 illustrated in FIG. 18. After generating a process schedule M4 as illustrated in FIG. 19, the schedule generation unit 54a compares the scheduled date and time of patient revisit (see a recording field m41) and image transfer start dates and times (see a recording field m42). Then, an image transfer start date and time later than the scheduled date and time of patient revisit is extracted. In the example in FIG. 19, an image transfer start date and time recorded in a recording field m43 (Feb. 3, 2012, 18:45) is later than the scheduled date and time of patient revisit (Feb. 3, 2012, 18:15).

When the image transfer start date and time later than the scheduled date and time of patient revisit is extracted, the schedule generation unit 54a modifies the process schedule so that image data corresponding to the observation purpose associated with the extracted image transfer start date and time is not transferred.

At subsequent Step S13, the inspection management apparatus 5 initializes the receiving device 3, and registers, together with the examination information and the patient information, the observation schedule information in the receiving device 3 according to the modified process schedule. FIG. 20 is a table illustrating an example of the observation schedule information registered in the receiving device 3. In observation schedule information M5 illustrated in FIG. 20, a target image (entire image) that was scheduled to be transferred on Feb. 3, 2012 at 18:45 in the process schedule M4 illustrated in FIG. 19 is deleted.

Subsequent Steps S14 to S22 are the same as those of the first embodiment.

When the patient revisits the hospital and the examination ends (see Step S22), the user removes the receiving device 3 from the subject 10 and connects the receiving device 3 to the inspection management apparatus 5 via the cradle 3a. In response to this, at Step S23, the receiving device 3 transfers, to the inspection management apparatus 5, image data that have not been transferred. These image data include image data corresponding to the observation purpose of "entire image observation" (see FIG. 19). Subsequent processes are the same as those of the first embodiment.

As described above, according to the second embodiment, when a patient is in a hospital and communication between the receiving device 3 and the inspection management apparatus 5 via a USB is enabled, image data is transferred by the communication using the USB. Therefore, it becomes possible to prevent other communication lines from being squeezed. As a spin-off effect, it becomes possible to prevent consumption of the battery 40 of the receiving device 3, enabling to reduce a risk that the power of the receiving device 3 may be run out during image capturing.

Third Embodiment

Next, a third embodiment of the present invention will be described.

Figure 21:
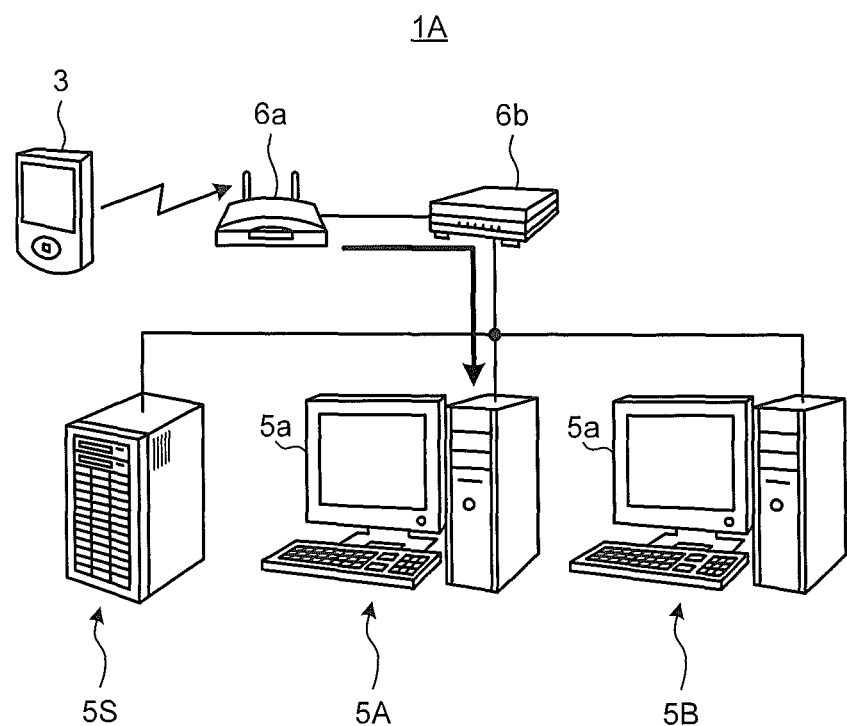
FIG. 21 is a schematic diagram illustrating a schematic configuration of an inspection management system according to a third embodiment of the present invention.

FIG. 21 is a schematic diagram illustrating a schematic configuration of an inspection management system according to the third embodiment. An inspection management system 1A according to the third embodiment includes: the receiving device 3 that receives wireless signals wirelessly transmitted from the capsule endoscope 2 (see FIG. 1) via the receiving antenna unit 4 attached to the subject 10 (see FIG. 1); a plurality of clients 5A and 5B that receive image data transmitted from the receiving device 3 via a receiving antenna 6a and a router 6b and performs specified image processing on the received image data; and a server 5S that records the image data processed by each of the clients 5A and 5B. If a plurality of the subjects 10 are to be examined in parallel, a plurality of the receiving devices 3 are provided in accordance with a plurality of the capsule endoscopes 2 to be swallowed by the respective subjects 10.

Each of the clients 5A and 5B is configured by using a workstation including the display device 5a similarly to the inspection management apparatus 5 of the first embodiment. The configuration and operation of each of the clients 5A and 5B are the same as those of the inspection management apparatus 5 illustrated in FIG. 3.

The server 5S integrally manages various data, such as the patient information, the examination information, the observation schedule information, and image data subjected to the image processing by each of the clients 5A and 5B, which are generated through operation related to a series of capsule endoscopic examinations performed by the inspection management system 1A.

Next, operation of the inspection management system 1A will be described with reference to FIG. 12. In the description below, an example will be described in which a user inputs various information on the inspection management system 1A by using the client 5A; however, the same applies to the case where the client 5B is used.

First, at Step S10, the client 5A displays the observation schedule setting screen on the display device 5a. FIG. 22 is a schematic diagram illustrating an example of the observation schedule setting screen. In an observation schedule setting screen M6 illustrated in FIG. 22, a display and selection field m61 for a client workstation (WS) name is provided in addition to the fields in the observation schedule setting screen M1 illustrated in FIG. 13. The display and selection field m61 displays a drop-down list of names (WS_A and WS_B) for identifying the clients 5A and 5B connected to the inspection management system 1. A user is able to select a displayed name to designate the client 5A or 5B, to which image data is transferred from the receiving device 3 and which is caused to execute image processing on the image data. In FIG. 22, the client WS name is selected such that the client 5A (the client WS name: WS_A) performs processing on image data related to an examination of one subject (a patient name ZZZ) and the client 5B (the client WS name: WS_B) performs processing on image data related to an examination of another subject (a patient name YYY).

While the observation schedule setting screen M6 is being opened in the client 5A, it is preferable to open the same screen only in a read-only mode in other terminals (the client 5B and the like) in order to prevent the observation schedule from being edited simultaneously.

At Step S11, the client 5A receives input of setting information including the scheduled swallowing date and time, the scheduled start date and time of observation, the observation purpose, and the client WS name. Furthermore, the client 5A transmits the received setting information to the server 5S.

At subsequent Step S12, the client 5A calculates an image transfer start date and time and an image processing start date and time for each observation purpose based on the received setting information, and generates a process schedule. The procedure for generating the process schedule is the same as the first embodiment.

Figures 23, 24:
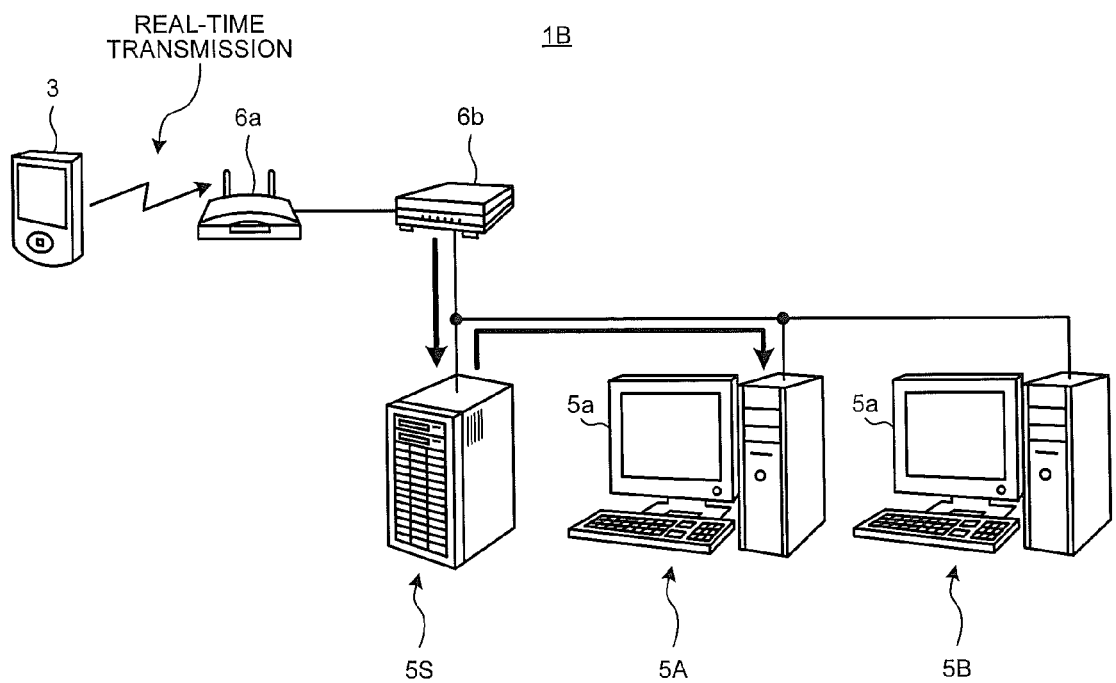
FIG. 23 is a table illustrating an example of observation schedule information registered in a receiving device illustrated in FIG. 21.
FIG. 24 is a schematic diagram illustrating a schematic configuration of an inspection management system according to a fourth embodiment of the present invention.

When the receiving device 3 is connected to each of the clients 5A and 5B via the cradle 3a, each of the clients 5A and 5B initializes the receiving device 3 and registers the examination information, the patient information, and the observation schedule information at Step S13. FIG. 23 is a table illustrating an example of the observation schedule information registered in the receiving device 3 connected to the client 5A. Observation schedule information M7 illustrated in FIG. 23 contains, in addition to the information on the image transfer start date and time and the target image, client WS identification information for identifying a client serving as a transfer destination of the image data. The client WS identification information is, in particular, a computer name (name), an IP address, or the like. Each of the clients 5A and 5B acquires the client WS identification information as described above from information set in an OS thereof.

Subsequent Steps S14 to S22 are the same as those of the first embodiment. During these processes, each of the receiving devices 3 transmits specified image data to the designated client 5A or 5B according to the registered observation schedule information. Furthermore, each of the clients 5A and 5B performs specified image processing on the received image data according to the process schedule.

After the examination of each of the subjects (for example, the patient names ZZZ and YYY) ends, if the receiving device 3 is connected to each of the clients 5A and 5B via the cradle 3a, each of the receiving devices 3 transfers remaining image data to the client 5A or 5B, and each of the clients 5A and 5B performs specified image processing on the received image data at Step S23.

As described above, according to the third embodiment, even when the inspection management system 1A includes the server 5S and the plurality of the clients 5A and 5B, each of the receiving devices 3 is able to transfer image data to the designated client 5A or 5B based on the client WS identification information.

Furthermore, according to the third embodiment, the server 5S integrally manages data (the setting information or the like) input in each of the clients 5A and 5B; therefore, it becomes possible to confirm, from both of the clients 5A and 5B, what observation schedules are made by the clients 5A and 5B. Furthermore, if the clients 5A and 5B are installed in rooms of respective users (observation doctors), it becomes possible to perform sorting to determine what data is to be observed by which user. Therefore, it becomes possible to distribute loads between users, enabling to improve the convenience.

Fourth Embodiment

Next, a fourth embodiment of the present invention will be described.

FIG. 24 is a schematic diagram illustrating a schematic configuration of an inspection management system according to the fourth embodiment. As illustrated in FIG. 24, an inspection management system 1B according to the fourth embodiment includes: the receiving device 3 that receives wireless signals wirelessly transmitted from the capsule endoscope 2 (see FIG. 1) via the receiving antenna unit 4; the server 5S that receives image data transmitted from the receiving device 3 via the receiving antenna 6a and the router 6b; and the plurality of the clients 5A and 5B each performing image processing on image data transferred from the server 5S.

The server 5S integrally manages various data, such as the patient information, the examination information, the observation schedule information, and image data subjected to the image processing by each of the clients 5A and 5B, which are generated through operation related to a series of capsule endoscopic examinations performed by the inspection management system 1B.

Each of the clients 5A and 5B is configured by using a workstation including the display device 5a similarly to the third embodiment. The configuration and operation of each of the clients 5A and 5B are the same as those of the inspection management apparatus 5 illustrated in FIG. 3.

Next, operation of the inspection management system 1B will be described with reference to FIG. 12. In the description below, a user inputs various information on the inspection management system 1B by using the client 5A; however, the same applies to the case where the client 5B is used.

First, at Step S10, the client 5A displays the observation schedule setting screen on the display device 5a (see FIG. 22).

At subsequent Step S11, the client 5A receives input of setting information including the scheduled swallowing date and time, the scheduled start date and time of observation, the observation purpose, and the client WS name. Furthermore, the client 5A transmits the received setting information to the server 5S.

At subsequent Step S12, the client 5A calculates an image transfer start date and time and an image processing start date and time for each observation purpose based on the received setting information, and generates a process schedule. The procedure for generating the process schedule is the same as the first embodiment. However, as a transfer time (seconds per image) used to calculate the image transfer start date and time, a statistic of a transfer time between each of the clients 5A and 5B and the server 5S is used. This statistic may be calculated based on past processing results, or it may be possible to set an initial value in advance based on test results obtained in the development.

Figures 25, 26:
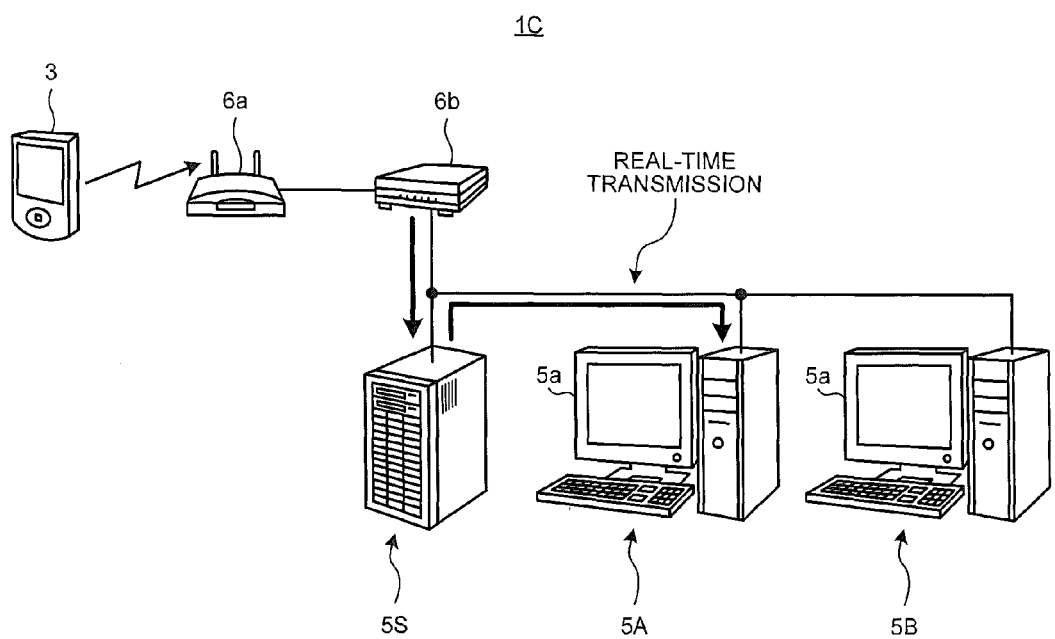
FIG. 25 is a table illustrating an example of a process schedule registered in a server illustrated in FIG. 24.
FIG. 26 is a schematic diagram illustrating a schematic configuration of an inspection management system according to a fifth embodiment of the present invention.

Furthermore, each of the clients 5A and 5B registers the generated process schedule in the server 5S. FIG. 25 is a table illustrating an example of the process schedule registered in the server 5S. In the process schedule, the image transfer start date and time, the client WS name for identifying the client 5A or 5B serving as a transfer destination, and an observation purpose are recorded.

When the receiving device 3 is connected to each of the clients 5A and 5B via the cradle 3a, each of the clients 5A and 5B initializes the receiving device 3 and registers the examination information and the patient information at Step S13. In this case, it may be possible to additionally register identification information (a computer name, an IP address, or the like) for identifying the server 5S.

Thereafter, when the examination is started at Step S14, the receiving device 3 accumulates image data received from the capsule endoscope 2 in the memory 33, and transmits the received image data to the server 5S via an available communication line or the like in real time.

At Step S15, the server 5S determines whether the image transfer start date and time set for each observation purpose has passed based on the process schedules registered by the clients 5A and 5B. If the image transfer start date and time has passed (Step S15: Yes), the server 5S determines image data corresponding to the observation purpose, and transfers the image data to the client identified by the client WS name (Step S17). If the image transfer start date and time has not already passed (Step S15: No), the server 5S waits until the image transfer start date and time has passed (Step S16).

Subsequent processes at and after Step S18 are the same as those of the third embodiment.

Modified Example

In the above described fourth embodiment, when the process schedules registered in the server 5S and the image transfer start date and time comes, the server 5S transfers specified image data to the specified client 5A or 5B according to the process schedule. However, it may be possible to cause each of the clients 5A and 5B to acquire image data from the server 5S when the image transfer start date and time comes.

Fifth Embodiment

Next, a fifth embodiment of the present invention will be described.

FIG. 26 is a schematic diagram illustrating a schematic configuration of an inspection management system according to the fifth embodiment. As illustrated in FIG. 26, an inspection management system 1C according to the fifth embodiment includes, similarly to the third embodiment: the server 5S that receives image data transmitted from the receiving device 3 via the receiving antenna 6a and the router 6b; and the plurality of the clients 5A and 5B each performing specified image processing on image data transferred from the server 5S. A feature is that each of the clients 5A and 5B acquires, in real time, the image data that the server 5S has received from the receiving device 3.

Operation of the inspection management system 1C will be described with reference to FIG. 12.

First, each of the clients 5A and 5B calculates an image transfer start date and time and an image processing start date and time for each observation purpose, and generates a process schedule in the same manner as in Steps S10 to S12 of the third embodiment. In this case, as a transfer time (seconds per image) used to calculate the image transfer start date and time, a value is used, which is obtained by adding a statistic of a transfer time between each of the clients 5A and 5B and the server 5S to a statistic (see FIG. 6) of the image transfer necessary time that is determined according to the communication method used to transfer image data from the receiving device 3 to the server 5S. These statistics may be calculated based on examinations performed in the past in the inspection management system 1C, or it may be possible to set an initial value in advance based on test results obtained in the development.

When the receiving device 3 is connected to each of the clients 5A and 5B via the cradle 3a, each of the clients 5A and 5B initializes the receiving device 3 and registers the examination information, the patient information, and the observation schedule information at Step S13. In this case, it may be possible to additionally register, in the observation schedule information, identification information (a computer name, an IP address, or the like) for identifying the server 5S and identification information for identifying each of the clients 5A and 5B serving as a final transfer destination.

Thereafter, when the examination is started at Step S14, the receiving device 3 accumulates image data received from the capsule endoscope 2 in the memory 33.

At Step S15, the receiving device 3 determines whether the image transfer start date and time set for each observation purpose has passed, based on the observation schedule information. If the image transfer start date and time has passed (Step S15: Yes), the receiving device 3 determines image data corresponding to the observation purpose, and transmits the image data to the server 5S via an available communication line or the like, and, the server 5S transfers the received image data to the clients 5A and 5B in real time (Step S17). The receiving device 3 may add identification information for identifying each of the clients 5A and 5B serving as a final transfer destination to the image data when transmitting the image data. In this case, the server 5S is able to determine the transfer destination of the image data based on the identification information added to the image data. If the image transfer start date and time has not already passed (Step S15: No), the server 5S waits until the image transfer start date and time has passed (Step S16).

The subsequent processes at and after Step S18 are the same as those of the third embodiment.

Sixth Embodiment

Next, a sixth embodiment of the present invention will be described.

A feature of the sixth embodiment is that the receiving device 3 determines a date and time at which the subject 10 has actually swallowed the capsule endoscope 2, and an inspection management apparatus modifies a process schedule based on the actual swallowing date and time. The configuration of an inspection management apparatus according to the sixth embodiment is the same as illustrated in FIG. 3. Furthermore, the entire configuration of the inspection management system is the same as illustrated in FIG. 1.

Figure 27:
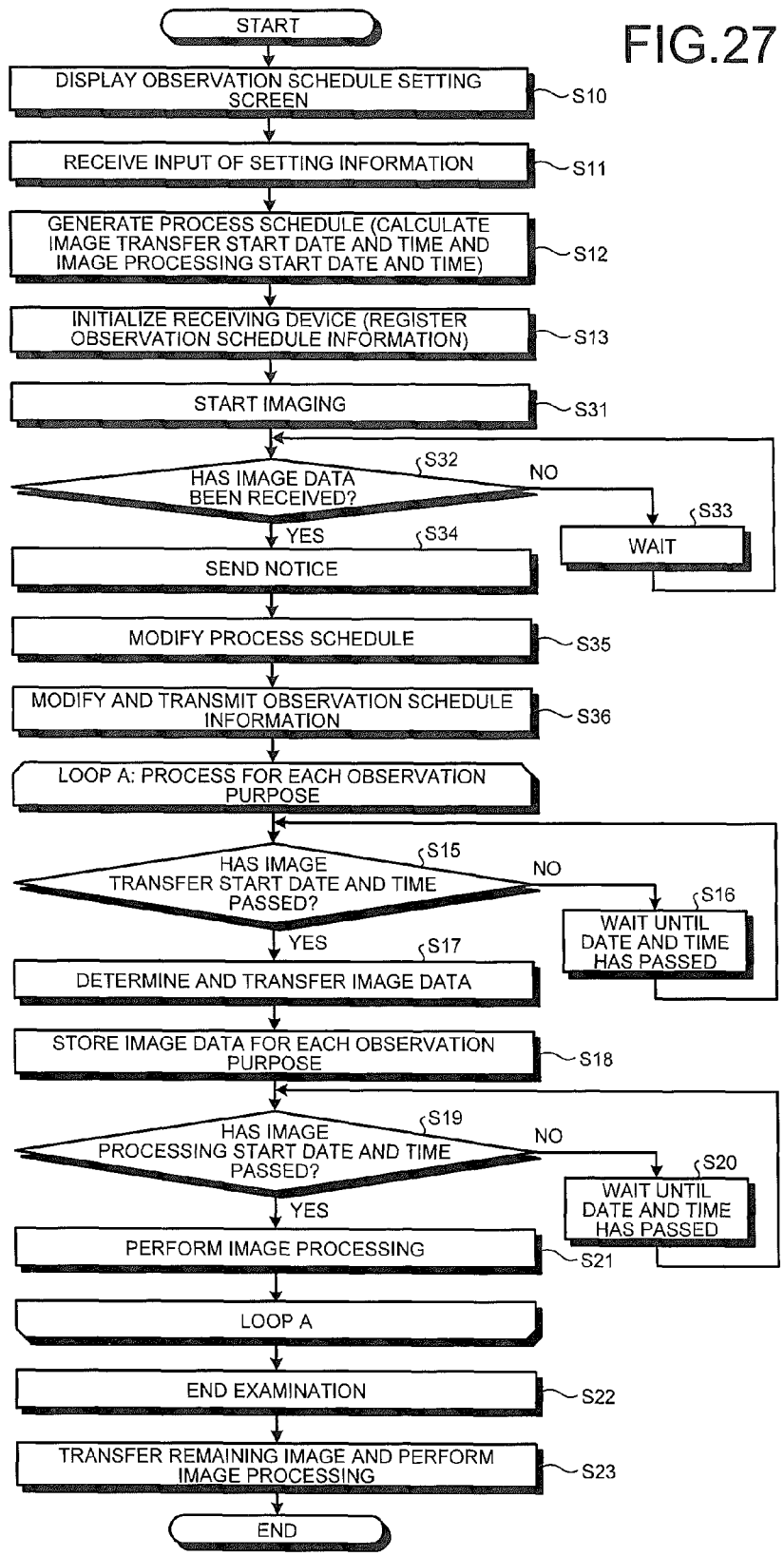
FIG. 27 is a flowchart illustrating operation of an inspection management system according to a sixth embodiment of the present invention.

FIG. 27 is a flowchart illustrating operation of the inspection management system according to the sixth embodiment. The operations from Steps S10 to S13 are the same as those of the first embodiment.

After Step S13, when the user turns on the power supply of the capsule endoscope 2, the capsule endoscope 2 starts imaging and wirelessly transmits image data to the receiving device 3 at Step S31.

At Step S32, the receiving device 3 determines whether image data has been received from the capsule endoscope 2. If the image data has not already been received (Step S32: No), the receiving device 3 waits until the image data is received (Step S33).

In contrast, if the image data has been received (Step S32: Yes), the receiving device 3 notifies the inspection management apparatus 5 of the reception of the image data and the imaging date and time of a first image via an available communication line or the like (Step S34).

At Step S34, when the inspection management apparatus 5 receives the notice from the receiving device 3, the schedule generation unit 54a modifies the process schedule generated at Step S12, by employing the imaging date and time of the first image as a swallowing date and time (see FIG. 14) (Step S35). That is, the image transfer start date and time and the image processing start date and time are recalculated so as to be in time for the initially set scheduled start date and time of observation based on the new swallowing date and time.

Furthermore, at Step S36, the inspection management apparatus 5 modifies the observation schedule information registered in the receiving device 3 at Step S13 (see FIG. 16), and transmits the modified observation schedule information to the receiving device 3 via an available communication line or the like to reregister the observation schedule information in an overwriting manner.

Subsequent operation after the loop A is the same as the first embodiment.

As described above, according to the sixth embodiment, even when the scheduled swallowing date and time is shifted, the process schedule is modified by employing the image capturing start date and time of the capsule endoscope 2 as the swallowing date and time. Therefore, it becomes possible to manage schedules in accordance with the reality.

Seventh Embodiment

Next, a seventh embodiment of the present invention will be described.

In the above described sixth embodiment, the process schedule is modified by employing the date and time at which the capsule endoscope 2 captures a first image as the swallowing date and time. However, in some cases, test images may be captured after the power supply of the capsule endoscope 2 is turned on and image capturing operation is started, and there may be a time lag until the subject 10 actually swallows the capsule endoscope 2. Therefore, a feature of the seventh embodiment is that the process schedule is modified by employing a date and time at which the capsule endoscope 2 captures a first image of inside of the subject 10 as the swallowing date and time. The configuration of an inspection management apparatus according to the seventh embodiment is the same as illustrated in FIG. 3. The entire configuration of the inspection management system is the same as illustrated in FIG. 1.

Figure 28:
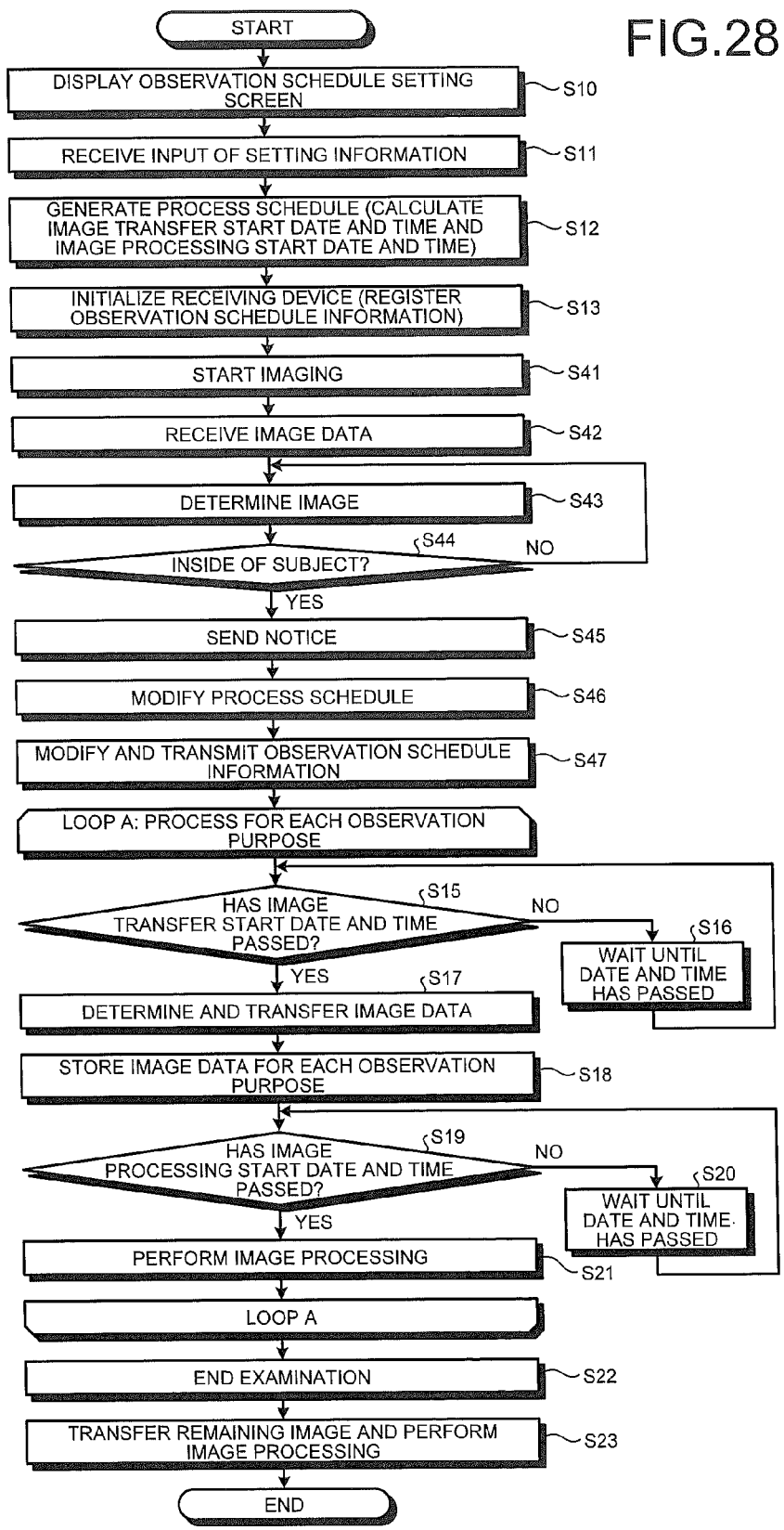
FIG. 28 is a flowchart illustrating operation of an inspection management system according to a seventh embodiment of the present invention.

FIG. 28 is a flowchart illustrating operation of the inspection management system according to the seventh embodiment. Steps S10 to S13 are the same as those of the first embodiment.

After Step S13, when a user turns on the power supply of the capsule endoscope 2, the capsule endoscope 2 starts imaging and wirelessly transmits image data to the receiving device 3 at Step S41.

At Step S42, the receiving device 3 receives the image data from the capsule endoscope 2. At Step S43, the image determination unit 34 (see FIG. 2) performs image determination process to determine whether the received image data has been obtained by imaging the inside of the subject 10. As the image determination process, for example, a process of calculating an average color of the image is performed. In this case, if the average color is reddish, the image data can be determined as having been obtained by imaging the inside of the subject.

If the image data is not determined as having been obtained by imaging the inside of the subject (Step S44: No), the receiving device 3 repeats image processing on image data sequentially and wirelessly transmitted from the capsule endoscope 2 (Step S43).

In contrast, if the image data is determined as having been obtained by imaging the inside of the subject (Step S44: Yes), the receiving device 3 notifies the inspection management apparatus 5 of the start of the imaging of the inside of the subject and the imaging date and time of first image data determined as having been obtained by imaging the inside of the subject, via an available communication line or the like (Step S45).

At Step S45, when the inspection management apparatus 5 receives the notice from the receiving device 3, the schedule generation unit 54a modifies the process schedule (see FIG. 14) generated at Step S12, by employing, as the swallowing date and time, the imaging date and time of the first image data determined as having been obtained by imaging the inside of the subject (Step S46). That is, the image transfer start date and time and the image processing start date and time are recalculated so as to be in time for the initially set scheduled start date and time of observation based on the new swallowing date and time.

Furthermore, at Step S47, the inspection management apparatus 5 modifies the observation schedule information (see FIG. 16) registered in the receiving device 3 at Step S13, and transmits the modified observation schedule information to the receiving device 3 via an available communication line or the like to reregister the observation schedule information in an overwriting manner.

Subsequent operation after the loop A is the same as the first embodiment.

As described above, according to the seventh embodiment, the process schedule is modified by employing, as the swallowing date and time, a date and time at which imaging of the inside of the subject 10 is actually started. Therefore, it becomes possible to further mange schedules in accordance with the reality.

Eighth Embodiment

Next, an eighth embodiment of the present invention will be described.

In the above described seventh embodiment, the receiving device 3 determines whether the image data has been obtained by imaging the inside of the subject. In contrast, in the eighth embodiment, this determination is performed by the inspection management apparatus 5 illustrated in FIG. 3. The entire configuration of an inspection management system is the same as illustrated in FIG. 1.

Figure 29:
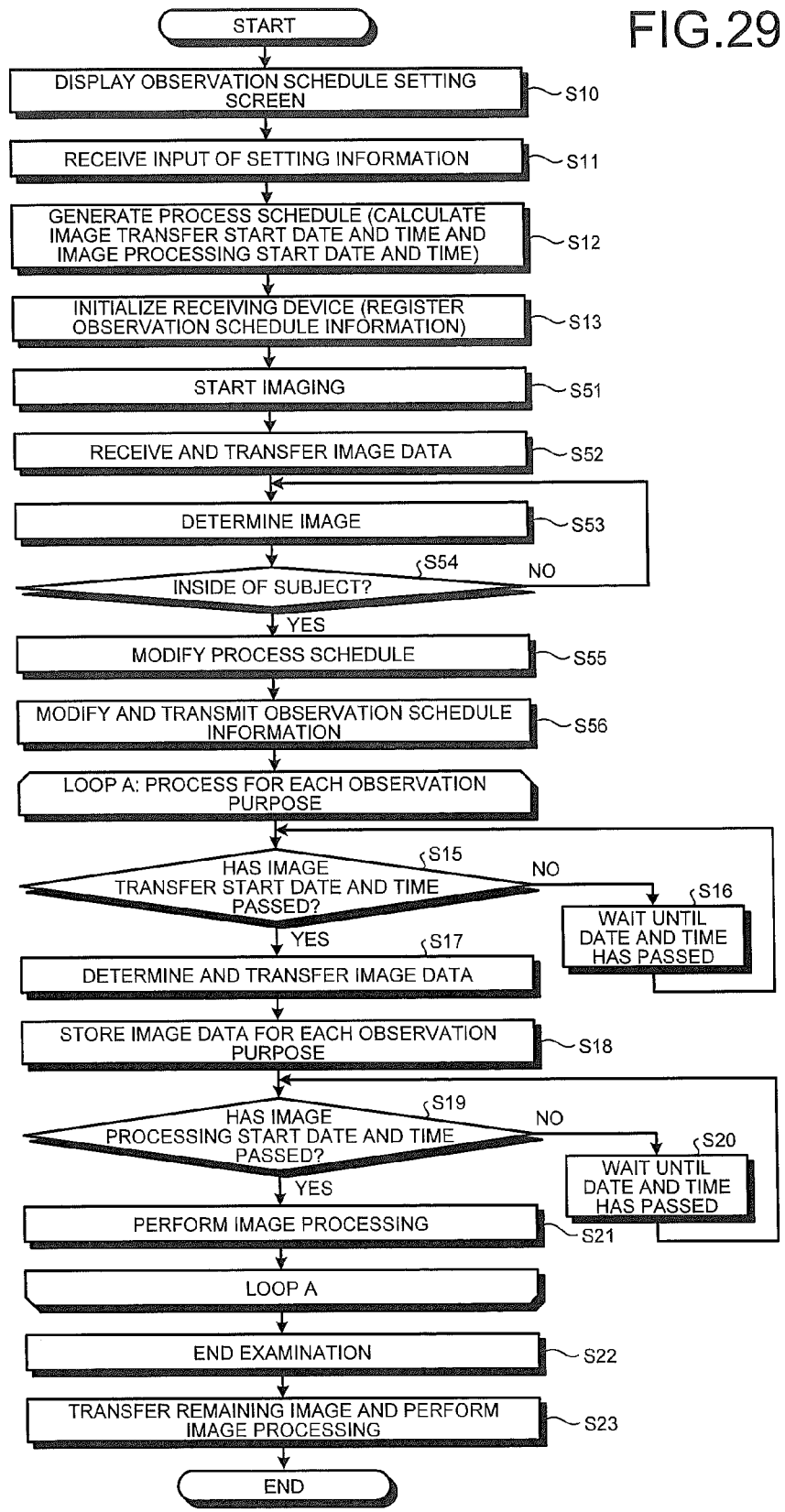
FIG. 29 is a flowchart illustrating operation of an inspection management system according to an eighth embodiment of the present invention.

FIG. 29 is a flowchart illustrating operation of the inspection management system according to the eighth embodiment. Steps S10 to S13 are the same as those of the first embodiment.

After Step S13, when a user turns on the power supply of the capsule endoscope 2, the capsule endoscope 2 starts imaging and wirelessly transmits image data to the receiving device 3 at Step S51.

At Step S52, the receiving device 3 receives image data from the capsule endoscope 2 and transfers the received image data to the inspection management apparatus 5 via an available communication line or the like in real time.

At Step S53, the image processing unit 54b performs the image determination process to determine whether the received image data is obtained by imaging the inside of the subject 10. As the image determination process, for example, a process of calculating an average color of the image is performed. In this case, if the average color is reddish, the image data can be determined as having been obtained by imaging the inside of the subject.

If the image data is not determined as having been obtained by imaging the inside of the subject (Step S54: No), the image processing unit 54b repeats image processing on image data sequentially transmitted from the receiving device 3 (Step S53).

In contrast, if the image data is determined as having been obtained by imaging the inside of the subject (Step S54: Yes), the schedule generation unit 54a modifies the process schedule (see FIG. 14) generated at Step S12, by employing, as the swallowing date and time, the imaging date and time of the first image data determined as having been obtained by imaging the inside of the subject (Step S55). That is, the image transfer start date and time and the image processing start date and time are recalculated so as to be in time for the initially set scheduled start date and time of observation based on the new swallowing date and time. Incidentally, when the image data is determined as having been obtained by imaging the inside of the subject, the inspection management apparatus 5 may transmit, to the receiving device 3, an instruction to suspend real time transfer of image data in order to start to transfer the image data after the image transfer start date and time based on the observation schedule comes.

Furthermore, at Step S56, the inspection management apparatus 5 modifies the observation schedule information (see FIG. 16) registered in the receiving device 3 at Step S13, and transmits the modified observation schedule information to the receiving device 3 via an available communication line or the like to reregister the observation schedule information in an overwriting manner.

Subsequent operation after the loop A is the same as the first embodiment.

As described above, according to the eighth embodiment, the inspection management apparatus 5 determines whether the image data is obtained by imaging the inside of the subject. Therefore, it becomes possible to reduce processing loads on the receiving device 3.

Ninth Embodiment

Next, a ninth embodiment of the present invention will be described.

In the above described first embodiment, the observation schedule information (see FIG. 16) is registered in the receiving device 3 based on the process schedule (see FIG. 14) generated by the inspection management apparatus 5, and the receiving device 3 starts to transfer image data when the image transfer start date and time comes. However, a command to start to transfer the image data may be issued from the inspection management apparatus 5 side.

In this case, at Step S12 illustrated in FIG. 12, the inspection management apparatus 5 initializes the receiving device 3 and registers, as the observation schedule information, information on a target image corresponding to the observation purpose.

Furthermore, at Step S15, the inspection management apparatus 5 determines whether the image transfer start date and time has passed based on the generated process schedule. If the image transfer start date and time has passed (Step S15: Yes), the inspection management apparatus 5 transmits an image transfer start command, which contains information for identifying an image to be transferred, to the receiving device 3 via an available communication line or the like. The information for identifying an image to be transferred may be, for example, an observation schedule identification number (see display field m11 in FIG. 13) or the like.

Upon receiving the image transfer start command, the receiving device 3 determines image data corresponding to the designated image and transmits the image data to the inspection management apparatus 5 via an available communication line or the like.

According to the above described ninth embodiment, it becomes not necessary to register the image transfer start date and time when the receiving device 3 is initialized. Therefore, for example, even when the process schedule is modified as in the sixth to the eighth embodiments, it becomes not necessary to reregister the modified image transfer start date and time in the receiving device 3.

Tenth Embodiment

Next, a tenth embodiment of the present invention will be described.

A feature of the tenth embodiment is that an observation schedule can be changed in midstream after the receiving device 3 is initialized. The configuration of an inspection management apparatus according to the tenth embodiment is the same as illustrated in FIG. 3. The entire configuration of an inspection management system is the same as illustrated in FIG. 1.

Figure 30:
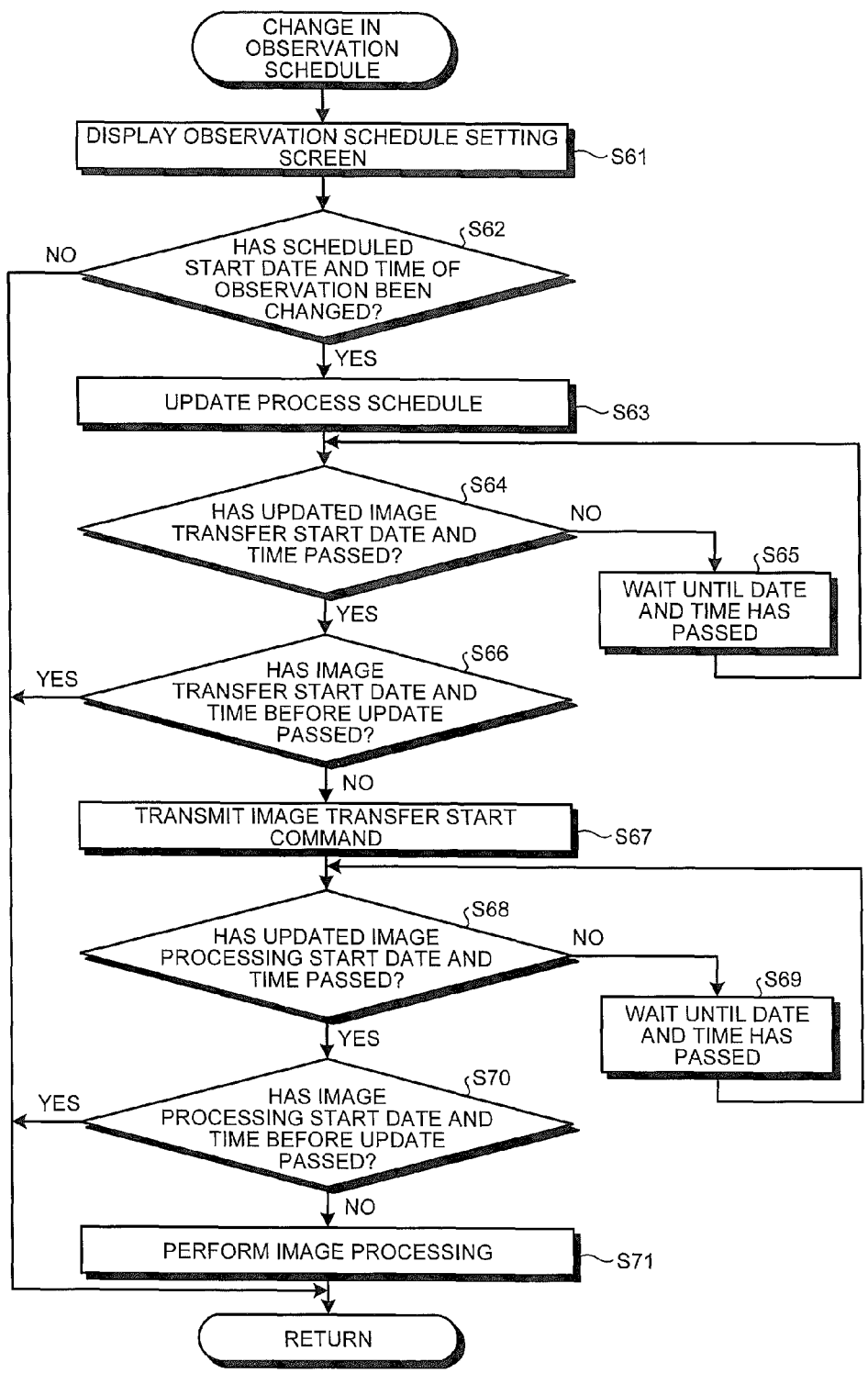
FIG. 30 is a flowchart illustrating operation related to a change in an observation schedule in an inspection management system according to a tenth embodiment of the present invention.

FIG. 30 is a flowchart illustrating operation related to a change in the observation schedule in the inspection management system according to the tenth embodiment. This operation is executable at any time after Step S13 illustrated in FIG. 12.

At Step S61, the inspection management apparatus 5 displays the observation schedule setting screen M1 illustrated in FIG. 13 on the display device 5a. It may be possible to display the observation schedule setting screen M1 according to input of operation by a user using the input unit 51. The user is able to change the scheduled start date and time of observation at any time by performing input operation on the observation schedule setting screen M1.

If the scheduled start date and time of observation has been changed (Step S62: Yes), the schedule generation unit 54a recalculates an image transfer start date and time and an image processing start date and time based on the changed scheduled start date and time of observation, and updates the process schedule (Step S63). In contrast, if the scheduled start date and time of observation has not been changed (Step S62: No), the operation returns to the main routine.

At Step S64, the inspection management apparatus 5 determines whether the updated image transfer start date and time has passed. If the updated image transfer start date and time has not already passed (Step S64: No), the inspection management apparatus 5 waits until the image transfer start date and time has passed (Step S65).

In contrast, if the updated image transfer start date and time has passed (Step S64: Yes), the inspection management apparatus 5 further determines whether the image transfer start date and time before the update has passed (Step S66). If the image transfer start date and time before the update has already passed (Step S66: Yes), namely, if the target image has already been transferred from the receiving device 3 to the inspection management apparatus 5, the operation directly returns to the main routine.

In contrast, if the image transfer start date and time before the update has not already passed (Step S66: No), the inspection management apparatus 5 transmits the image transfer start command to the receiving device 3 via an available communication line or the like (Step S67). In response to this, the receiving device 3 starts to transfer a target image to the inspection management apparatus 5.

At subsequent Step S68, the inspection management apparatus 5 determines whether the updated image processing start date and time has passed. If the updated image processing start date and time has not passed (Step S68: No), the inspection management apparatus 5 waits until the image processing start date and time has passed (Step S69).

In contrast, if the updated image processing start date and time has passed (Step S68: Yes), the inspection management apparatus 5 further determines whether the image processing start date and time before the update has already passed (Step S70). If the image processing start date and time before the update has already passed (Step S70: Yes), namely, if image processing on the target image has already started, the operation directly returns to the main routine.

In contrast, if the image processing start date and time before the update has not already passed (Step S70: No), the inspection management apparatus 5 starts to perform image processing on the target image (Step S71). Thereafter, the operation returns to the main routine.

As described above, according to the tenth embodiment, a user becomes able to change observation schedules at any time by performing input operation on the observation schedule setting screen M1.

Eleventh Embodiment

Next, a feature of an eleventh embodiment is that, similarly to the tenth embodiment, an observation schedule can be changed in midstream after the receiving device 3 is initialized. The configuration of an inspection management apparatus according to the eleventh embodiment is the same as illustrated in FIG. 3. The entire configuration of an inspection management system is the same as illustrated in FIG. 1.

Figure 31:
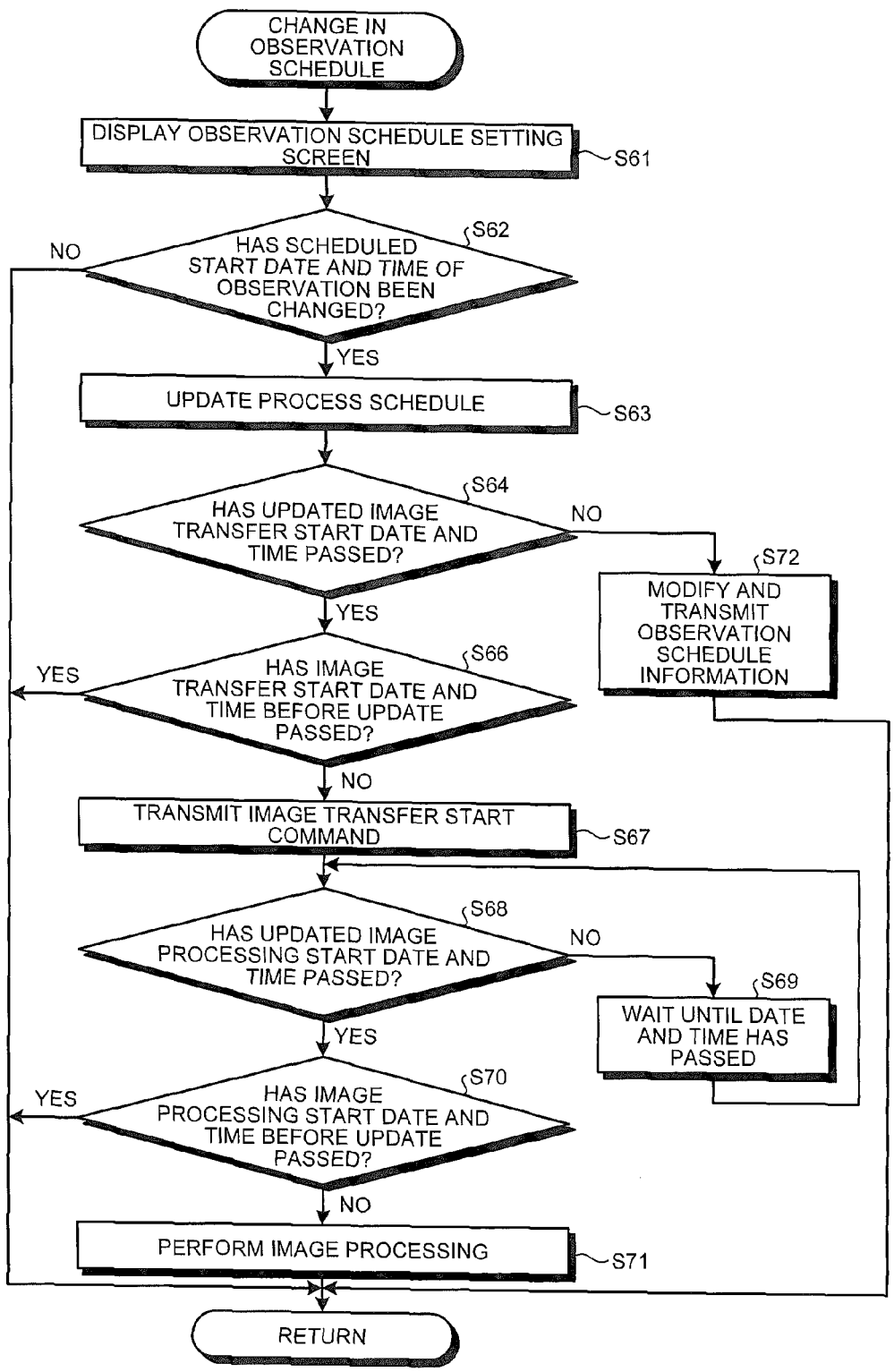
FIG. 31 is a flowchart illustrating operation related to a change in an observation schedule in an inspection management system according to an eleventh embodiment of the present invention.

FIG. 31 is a flowchart illustrating operation related to a change in the observation schedule in a capsule endoscopic system according to the eleventh embodiment. This operation is executable at any time after Step S13 illustrated in FIG. 12. Steps S61 to S64 and Steps S66 to S71 illustrated in FIG. 31 are the same as those of the tenth embodiment.

At Step S64, if the updated image transfer start date and time has not already passed (Step S64: No), the inspection management apparatus 5 modifies the observation schedule information (see FIG. 16) registered in the receiving device 3 at Step S13 (see FIG. 12), and transmits the modified observation schedule information to the receiving device 3 via an available communication line or the like to reregister the observation schedule information in an overwriting manner (Step S72). Thereafter, the operation returns to the main routine.

Even in the above described eleventh embodiment, a user becomes able to change observation schedules at any time by performing input operation on the observation schedule setting screen M1.

Twelfth Embodiment

Next, a twelfth embodiment of the present invention will be described.

Figure 32:
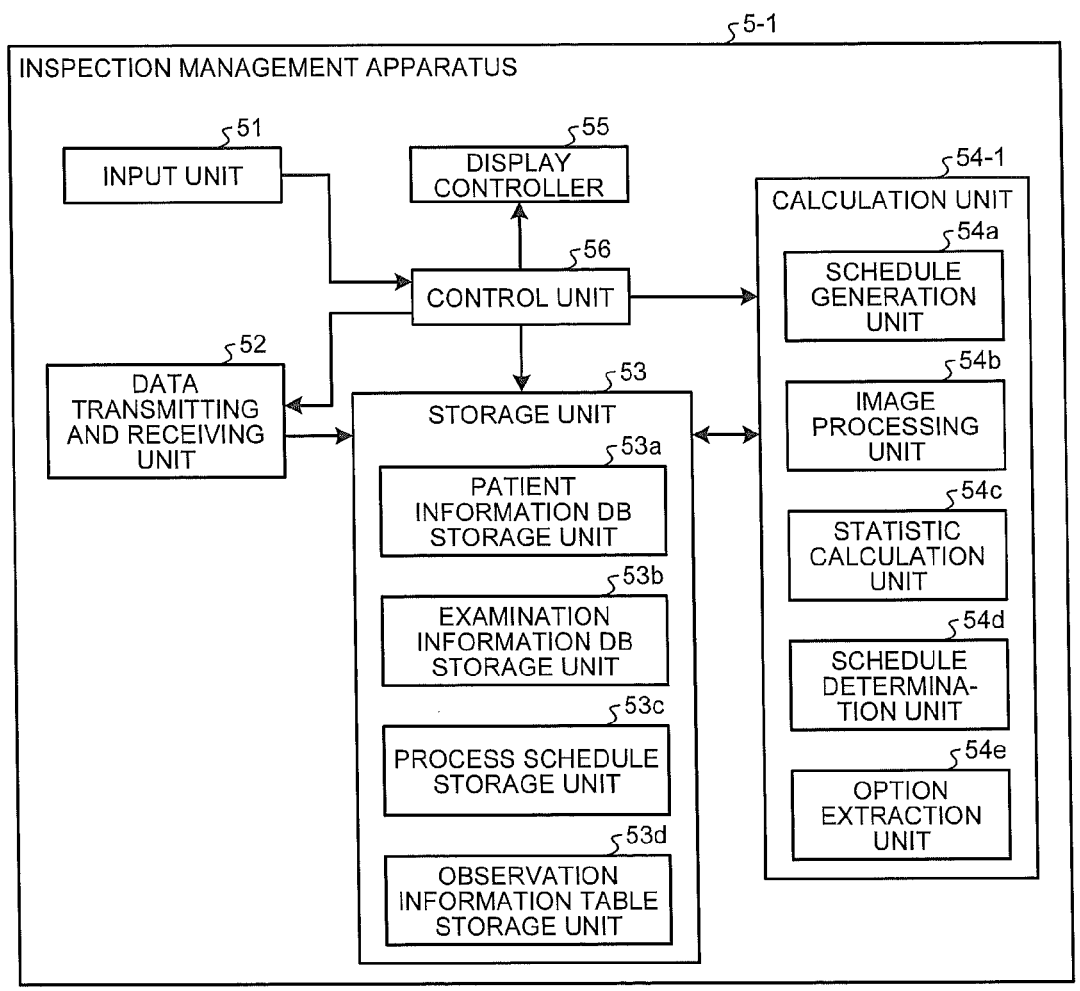
FIG. 32 is a block diagram illustrating a configuration of an inspection management apparatus according to a twelfth embodiment of the present invention.

FIG. 32 is a block diagram illustrating a configuration of an inspection management apparatus according to the twelfth embodiment. As illustrated in FIG. 32, an inspection management apparatus 5-1 according to the twelfth embodiment includes a calculation unit 54-1 that further includes a schedule determination unit 54d and an option extraction unit 54e in addition to the units of the calculation unit 54 illustrated in FIG. 3. The entire configuration of a capsule endoscopic system is the same as illustrated in FIG. 1.

In the above described first to ninth embodiments, in some cases, the process (transfer of image data and image processing) performed on an image to be observed may not be completed by the scheduled start date and time of observation set by the user, depending on a combination of the scheduled start date and time of observation and the observation purpose. Such a situation may occur when, for example, a time period from the scheduled swallowing date and time to the scheduled start date and time of observation is extremely short relative to the number of target images corresponding to the observation purpose, when a longer time is needed for image processing that is determined according to the observation purpose, or the like. Such a situation becomes obvious generally after the image transfer start date and time and the image processing start date and time are calculated.

Therefore, in the twelfth embodiment, the schedule determination unit 54d determines whether there is a possibility that a target image may not become observable by the scheduled start date and time of observation in the process schedule generated by the schedule generation unit 54a. When determining that there is such a possibility, the option extraction unit 54e extracts options selectable by a user depending on the situation. In response to this, the inspection management apparatus 5-1 displays, on the display device 5a, a message indicating that there is a possibility that the observation may be difficult to start on the set scheduled start date and time of observation, and the options extracted by the option extraction unit 54e. Situations (A) to (E) in which the observation may become difficult to start on the set scheduled start date and time of observation, and options (A-1) to (E-2) and their contents according to the respective situations will be described below.

(A) A situation where, while a certain target image group is being transferred, an image transfer start date and time of a next target image group set in the same examination comes.

(Option A-1) The image data are sequentially transferred from the target image group in order from the earliest image transfer start date and time. That is, this enables to infallibly start observations of target images in order from the earliest scheduled start date and time of observation.

(Option A-2) When a next image transfer start date and time comes, transfer of the next target image group is started. That is, the preceding target image group and the next target image group are transferred in parallel.

(Option A-3) A user is requested to modify the scheduled start date and time of observation.

(Option A-4) The image transfer start date and time is automatically adjusted. For example, the image transfer start date and time of a target image group corresponding to an earlier scheduled start date and time of imaging is brought forward.

(B) A situation where, while a certain target image group is being subjected to image processing, an image processing start date and time of a next target image group set in the same examination comes.

(Option B-1) Priority image processing is performed on target images in order from the earliest image processing start date and time. That is, this enables to infallibly start observations of target images in order from the earliest scheduled start date and time of observation.

(Option B-2) When a next image processing start date and time comes, image processing on the next target image group is started. That is, the preceding target image group and the next target image group are subjected to image processing in parallel.

(Option B-3) A user is requested to modify the scheduled start date and time of observation.

(Option B-4) The image transfer start date and time and the image processing start date and time are automatically adjusted. For example, the image processing start date and time of the target image group corresponding to an earlier scheduled start date and time of imaging is firstly brought forward. In this case, the image transfer start date and time of this target image group may also be brought forward if needed.

(C) A situation where image transfer start dates and times of two or more different examinations coincide with one another.

Such a situation may occur when examinations are performed on a plurality of the subjects 10 and a plurality of receiving devices attached to the respective subjects 10 transfer image data to a single inspection management apparatus.

(Option C-1) Image data of images of an examination corresponding to an earlier image transfer start date and time are preferentially transferred. For example, when a first image transfer start date and time of a first examination is earlier than a first image transfer start date and time of a second examination, and if the inspection management apparatus 5-1 receives image data transferred from a second receiving device used for the second examination while receiving image data transferred from a first receiving device used for the first examination, the inspection management apparatus 5-1 transmits an image transfer wait request to the second receiving device. In this case, the second receiving device retransfers the image data to the inspection management apparatus 5-1 after a lapse of a specified time (retry time) set in advance since reception of the image transfer wait request. At this time, if the transfer of the image data from the first receiving device to the inspection management apparatus 5-1 has ended, the inspection management apparatus 5-1 receives the image data transferred from the second receiving device. In this case, the inspection management apparatus 5-1 may update the image transfer start date and time set for the second receiving device with a date and time at which the transferred image is actually received. In contrast, if the transfer of the image data from the first receiving device has not ended, the inspection management apparatus 5-1 retransmits the image transfer wait request to the second receiving device.

Alternatively, when the transfer of the image data from the first receiving device ends after the inspection management apparatus 5-1 has transmitted the image transfer wait request to the second receiving device, the inspection management apparatus 5-1 may transmit an image transfer resume request to the second receiving device. In this case, the second receiving device need not retry transmission of the image data at specified time intervals, and only has to wait for the image transfer resume request.

The same applies to the case where image data are transferred from three or more receiving devices to the single inspection management apparatus 5-1.

(Option C-2) A user is requested to set priorities of a plurality of examinations, and image data acquired by an examination with a higher priority is preferentially transferred. That is, while image data is being transferred from a first receiving device used for a first examination with a higher priority, if a second receiving device used for a second examination with a lower priority than the second examination starts to transfer image data, the inspection management apparatus 5-1 transmits an image transfer wait request to the second receiving device. In this case, the second receiving device retries transfer of the image data at specified time intervals, similarly to the above described option C-1. If the transfer of the image data from the first receiving device has ended, the inspection management apparatus 5-1 receives the image data transferred from the second receiving device. If the transfer of the image data from the first receiving device has not ended, the inspection management apparatus 5-1 retransmits the image transfer wait request to the second receiving device. Alternatively, similarly to the above described option C-1, it may be possible to transmit an image transfer resume request from the inspection management apparatus 5-1 to the second receiving device after the transfer of images from the first receiving device has ended.

In contrast, when an image transfer start date and time for the first receiving device comes while images are being transferred from the second receiving device to the inspection management apparatus 5-1, the inspection management apparatus 5-1 transmits an image transfer wait request to the second receiving device and starts transfer of images from the first receiving device. After the transfer of the images from the first receiving device has ended, the image transfer resume request is transmitted to the second receiving device.

The same applies to the case where image data are transferred from three or more receiving devices to the single inspection management apparatus 5-1.

(Option C-3) Images are transferred to the inspection management apparatus in the order of the image transfer start date and time from the receiving devices corresponding to the respective examinations. That is, images are transferred from the plurality of the receiving devices in parallel.

(Option C-4) A user is requested to modify the scheduled start date and time of observation.

(Option C-5) The image transfer start date and time is automatically adjusted. For example, the image transfer start date and time in the examination corresponding to an earlier scheduled start date and time of imaging is brought forward.

(D) A situation where image processing start dates and times of two or more different examinations coincide with one another.

Such a situation may occur when examinations are performed on a plurality of the subjects 10 and image data transferred from receiving devices attached to the respective subjects 10 are processed by a single inspection management apparatus.

(Option D-1) Image processing is preferentially performed on images of an examination corresponding to an earlier image processing start date and time. For example, when the image processing start date and time of a first examination is earlier than the image processing start date and time of a second examination, even if the image processing start date and time of the second examination comes while image processing is being performed on a first image group acquired by the first examination, the inspection management apparatus 5-1 does not start to perform image processing on a second image group acquired by the second examination. That is, after the image processing on the first image group has ended, the image processing on the second image group is started. The same applies to the case where the single inspection management apparatus 5-1 performs image processing on image groups acquired by three or more examinations.

(Option D-2) A user is requested to set priorities of a plurality of examinations, and image processing is preferentially performed on an image group acquired by an examination with a higher priority. That is, while image processing is being performed on a first image group acquired by a first examination with a higher priority, even if the image processing start date and time corresponding to a second image group acquired by a second examination with a lower priority than the first examination comes, the inspection management apparatus 5-1 does not start image processing on the second image group. In this case, the inspection management apparatus 5-1 starts the image processing on the second image group after the image processing on the first image group has ended.

In contrast, when the image processing start date and time of the first image group comes while the image processing on the second image group is being performed, the inspection management apparatus 5-1 interrupts the image processing on the second image group and starts the image processing on the first image group. After the image processing on the first image group has ended, the image processing on the second image group is resumed.

The same applies to the case where the single inspection management apparatus 5-1 performs image processing on image groups acquired by three or more examinations.

(Option D-3) Image processing is started when the image processing start date and time comes with respect to any of image groups acquired by the respective examinations. That is, the plurality of the image groups are subjected to the image processing in parallel.

(Option D-4) A user is requested to modify the scheduled start date and time of observation.

(Option D-5) The image processing start date and time is automatically adjusted. For example, the image processing start date and time of an image group acquired by an examination corresponding to an earlier scheduled start date and time of imaging is brought forward. In this case, it may be possible to bring the image transfer start date and time of the same image group forward if needed.

(E) A situation where imaging of target images has not been completed by the image transfer start date and time.

(Option E-1) Transfer of the images is started after the imaging of the target images has ended. That is, the scheduled start date and time of observation is modified by giving a priority to observations of all target images.

(Option E-2) Only images that have been captured when the image transfer start date and time comes are transferred. That is, a priority is given to the scheduled start date and time of observation initially set by the user.

Thirteenth Embodiment

Next, a thirteenth embodiment of the present invention will be described.

Figure 33:
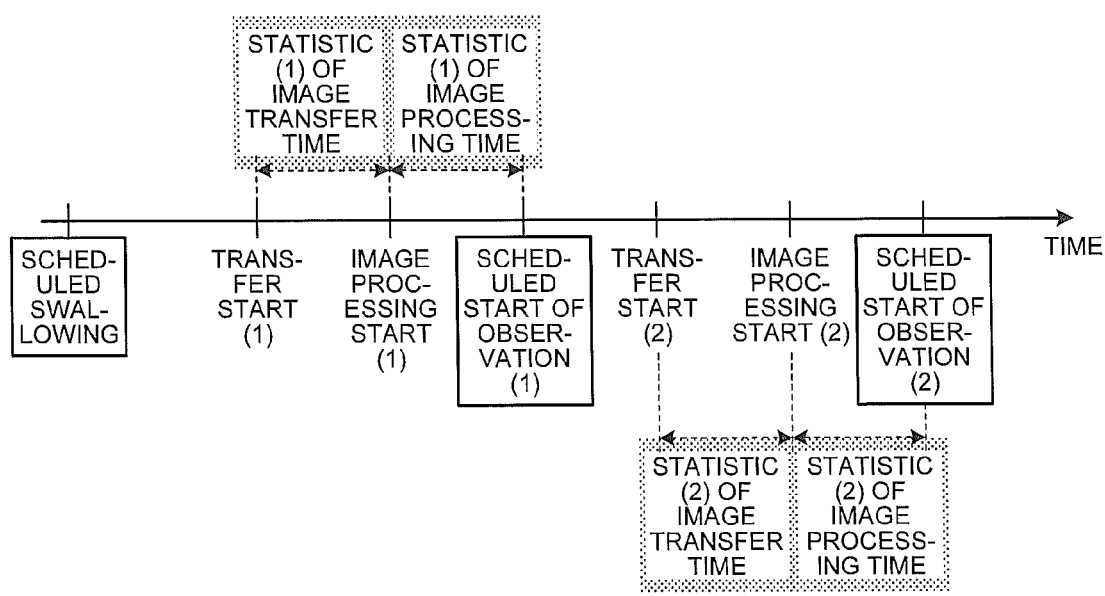
FIG. 33 is a diagram for explaining a method of calculating an image transfer start date and time and an image processing start date and time in an inspection management apparatus according to a thirteenth embodiment of the present invention.

In the above described first to ninth embodiments, the image transfer start date and time and the image processing start date and time are calculated by using the number of images, the statistic of the image transfer necessary time per image, the statistic of the image processing necessary time per image, and the like, based on the scheduled swallowing date and time and the scheduled start date and time of observation. In contrast, in the thirteenth embodiment, as illustrated in FIG. 33, statistics of the image transfer time and the image processing time are accumulated for each observation purpose, and the image transfer start date and time and the image processing start date and time are calculated based on the statistics. In FIG. 33, a statistic of an image transfer time (1) and a statistic of an image processing time (1), and, a statistic of an image transfer time (2) and a statistic of an image processing time (2) are illustrated according to the observation purposes.

Specifically, an image processing start date and time is calculated according to Equation (8) below, and an image transfer start date and time is calculated according to Equation (9) below using the calculated image processing start date and time.

(Image processing start date and time)=(Scheduled start date and time of observation)−(Statistic of mage processing time)  (8)

(Image transfer start date and time)=(Image processing start date and time)−(Statistic of image transfer time)  (9)

In this case, it becomes possible to simplify generation of a process schedule including calculations of the image transfer start date and time and the image processing start date and time.

If adequate statistics are not accumulated because the inspection management apparatus 5 has just been started to use, it may be possible to set only initial values based on test results obtained in the development of the inspection management apparatus 5.

Fourteenth Embodiment

Next, a fourteenth embodiment of the present invention will be described.

In the above described first to thirteenth embodiments, a user, such as a medical worker, has input the scheduled start date and time of observation in the inspection management apparatus 5. However, the inspection management apparatus 5 may set an appropriate scheduled start date and time of observation based on a work schedule of the medical worker, and may calculate an image transfer start date and time and an image processing start date and time according to the scheduled start date and time of observation.

In this case, the medical worker makes up a routine of a desired observation sequence and registers the routine in the inspection management apparatus 5 in advance. Therefore, the inspection management apparatus 5 becomes able to set observation purposes in the order corresponding to the registered routine, and to generate a process schedule based on the set observation purposes.

Fifteenth Embodiment

Next, a fifteenth embodiment of the present invention will be described.

Figure 34:
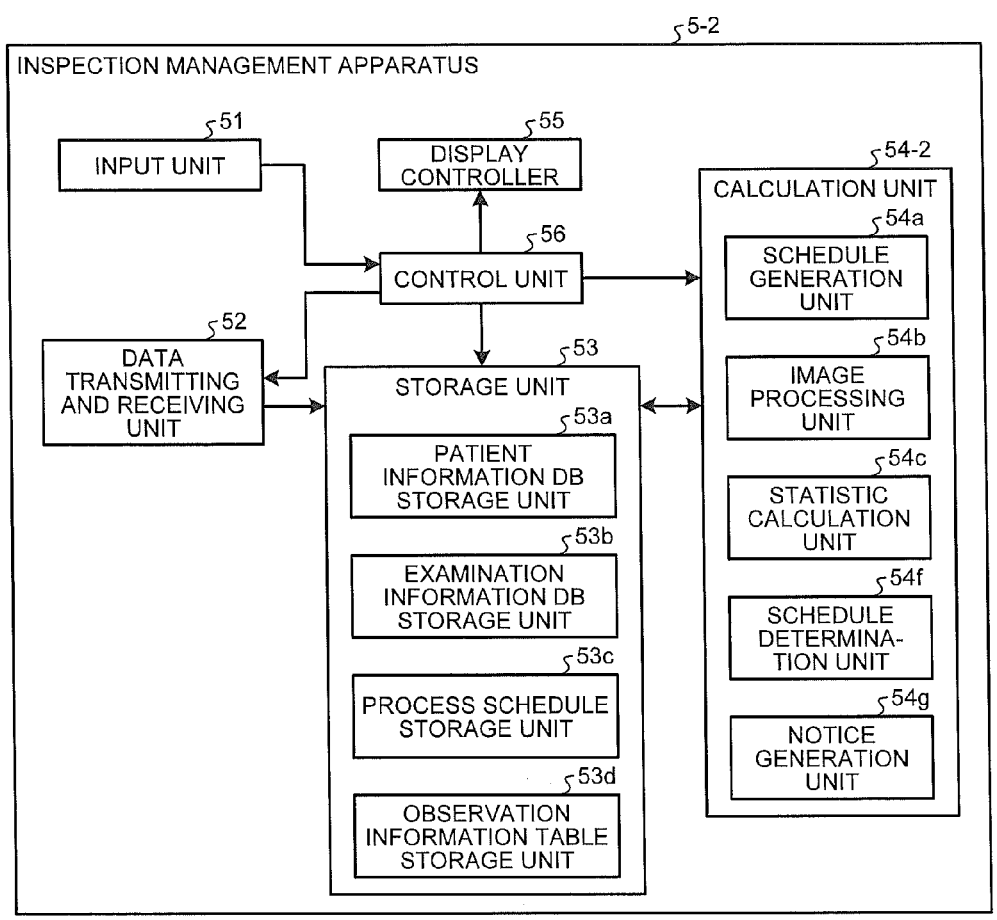
FIG. 34 is a block diagram illustrating a configuration of an inspection management apparatus according to a fifteenth embodiment of the present invention.

FIG. 34 is a block diagram illustrating a configuration of an inspection management apparatus according to the fifteenth embodiment. As illustrated in FIG. 34, an inspection management apparatus 5-2 according to the fifteenth embodiment includes a calculation unit 54-2 that further includes a schedule determination unit 54f and a notice generation unit 54g in addition to the units of the calculation unit 54 illustrated in FIG. 3. The entire configuration of a capsule endoscopic system is the same as the first embodiment.

When the schedule generation unit 54a generates a process schedule according to the scheduled swallowing date and time and the scheduled start date and time of observation input by the user, in some cases, the image transfer start date and time or the image processing start date and time may be earlier than the scheduled swallowing date and time. Therefore, the schedule determination unit 54f determines whether temporal consistency is maintained in the process schedule generated by the schedule generation unit 54a. If the consistency is not maintained (for example, the image transfer start date and time or the image processing start date and time is earlier than the scheduled swallowing date and time), the notice generation unit 54g generates a warning message indicating that a schedule is unable to be set. The inspection management apparatus 5-2 displays the warning message generated by the notice generation unit 54g on the display device 5a.

Sixteenth Embodiment

Next, a sixteenth embodiment of the present invention will be described.

As described in the first embodiment, the inspection management apparatus 5 generates a process schedule based on the statistics acquired from past results. Therefore, in some cases, transfer of image data from the receiving device 3 to the inspection management apparatus 5 or image processing performed by the inspection management apparatus 5 may end earlier than scheduled. Therefore, if the transfer of image data or the image processing ends earlier than scheduled, it may be possible to bring a start date and time of a subsequent process forward.

For example, setting is made in advance such that when the receiving device 3 ends transfer of images to the inspection management apparatus 5, an image transfer end notice is transmitted from the receiving device 3 to the inspection management apparatus 5. When receiving the image transfer end notice, the control unit 56 refers to the set process schedule and determines whether an image transfer process has ended earlier than scheduled. If the image transfer process has ended earlier than scheduled, the control unit 56 notifies the calculation unit 54 that the process has ended earlier. Therefore, the image processing unit 54b is able to start pre-set image processing at an earlier time.

Furthermore, when the image processing unit 54b ends the set image processing, the control unit 56 refers to the set process schedule and determines whether the image processing has ended earlier than scheduled. If the image processing has ended earlier than scheduled, the control unit 56 displays, on the display device 5a, a message indicating that the image processing has ended and an observation is available. Therefore, the user can start an observation before the scheduled start date and time of observation that he/she has set in advance.

As described above, according to the first to sixteenth embodiments, a date and time at which transfer of image data from the receiving device is started and a date and time at which image processing is started are calculated based on a scheduled start date and time of examination and a scheduled start date and time of observation input by a user. Therefore, a medical worker is able to start an observation of an image of a necessary area at a convenient timing.

The present invention is not limited to the first to sixteenth embodiments, and various inventions may be formed by appropriately combining a plurality of structural elements disclosed in the respective embodiments and modified examples. For example, formation by excluding some of the structural elements from the whole structural elements illustrated in the respective embodiments and modified examples may be made, or formation by appropriately combining the structural elements illustrated in the different embodiments and modified examples may be made. Furthermore, various modifications may be made according to specifications or the like, and it is obvious from the above descriptions that various other embodiments may be made within the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspection management apparatus for managing an examination performed in a capsule endoscopic system including a receiving device that receives image data from a capsule endoscope and stores the image data, the inspection management apparatus comprising:

a storage unit that stores a predictive transfer time which is a first predictive time needed to transfer the image data from the receiving device to the inspection management apparatus, and a predictive image processing time which is a second predictive time needed to perform image processing on the image data and set for each type of image processing;

an input unit that receives input of a first scheduled start date and time of the examination and a second scheduled start date and time of observation;

an image processing unit that performs image processing on the image data;

a schedule generation unit that, based on the first scheduled start date and time of the examination, the second scheduled start date and time of observation, the predictive transfer time, and the predictive image processing time, calculates an image transfer start date and time which is a date and time at which transfer of the image data from the receiving device to the inspection management apparatus is started, and calculates an image processing start date and time which is a date and time at which image processing is started on an image corresponding to the image data that the transfer has been started on the image transfer start date and time; and
a control unit that starts acquisition of the image data transmitted from the receiving device when the image transfer start date and time comes, and causes, when the image processing start date and time comes, the image processing unit to perform specified image processing on the image data that the transfer has been started on the image transfer start date and time.

2. The inspection management apparatus according to claim 1, further comprising a data transmitting and receiving unit that transmits and receives data to and from the receiving device, wherein
the control unit causes the data transmitting and receiving unit to transmit the image transfer start date and time to the receiving device.

3. The inspection management apparatus according to claim 1, further comprising a data transmitting and receiving unit that transmits and receives data to and from the receiving device, wherein
the control unit causes the data transmitting and receiving unit to transmit, to the receiving device on the image transfer start date and time, a notice indicating that the image transfer start date and time comes.

4. The inspection management apparatus according to claim 2, wherein
the input unit further receives input of information on an observation purpose,
the storage unit stores image data that the inspection management apparatus has received from the receiving device, and stores a table in which an observation target image according to the observation purpose and a type of image processing to be performed on the observation target image according to the observation purpose are associated with the observation purpose, and
the schedule generation unit calculates the image transfer start date and time and the image processing start date and time by using the observation target image and the type of image processing acquired from the table based on the information received by the input unit and by using the predictive transfer time and the predictive image processing time.

5. The inspection management apparatus according to claim 3, wherein
the input unit further receives input of information on an observation purpose,
the storage unit stores image data that the inspection management apparatus has received from the receiving device, and stores a table in which an observation target image according to the observation purpose and a type of image processing to be performed on the observation target image according to the observation purpose are associated with the observation purpose, and
the schedule generation unit calculates the image transfer start date and time and the image processing start date and time by using the observation target image and the type of image processing acquired from the table based on the information received by the input unit and by using the predictive transfer time and the predictive image processing time.

6. The inspection management apparatus according to claim 5, wherein the control unit causes the data transmitting and receiving unit to further transmit information on the observation target image to the receiving device.

7. The inspection management apparatus according to claim 5, wherein the control unit causes the image processing unit to perform image processing on the observation target image according to the observation purpose.

8. The inspection management apparatus according to claim 1, wherein the scheduled start date and time of the examination is a date and time at which the capsule endoscope is scheduled to be introduced into a subject.

9. The inspection management apparatus according to claim 1, wherein the schedule generation unit changes the scheduled start date and time of the examination based on data transmitted from the receiving device, and modifies the image transfer start date and time and the image processing start date and time based on the changed scheduled start date and time of the examination.

10. The inspection management apparatus according to claim 1, wherein the schedule generation unit updates the image transfer start date and time and the image processing start date and time based on the scheduled start date and time of observation that the input unit has received after the scheduled start date and time of the examination.

11. The inspection management apparatus according to claim 1, wherein
the input unit further receives input of a scheduled date and time of revisit for a patient who is a subject into which the capsule endoscope is configured to be introduced, and
when the image transfer start date and time is later than the scheduled date and time of revisit, the schedule generation unit updates the image transfer start date and time.

12. An inspection management system comprising:
an inspection management apparatus that manages an examination using a capsule endoscope; and
a receiving device that receives and stores image data transmitted from the capsule endoscope, and transfers at least a part of the image data to the inspection management apparatus, wherein
the inspection management apparatus includes:
a storage unit that stores a predictive transfer time which is a first predictive time needed to transfer the image data from the receiving device to the inspection management apparatus, and a predictive image processing time which is a second predictive time needed to perform image processing on the image data and set for each type of the image processing;
an input unit that receives input of a first scheduled start date and time of the examination and a second scheduled start date and time of observation;
an image processing unit that performs image processing on the image data;
a schedule generation unit that, based on the first scheduled start date and time of the examination, the second scheduled start date and time of observation, the predictive transfer time, and the predictive image processing time, calculates an image transfer start date and time which is a date and time at which transfer of the image data from the receiving device to the inspection management apparatus is started, and calculates an image processing start date and time which is a date and time at which image processing is started on an image corresponding to the image data that the transfer has been started on the image transfer start date and time; and
a control unit that starts acquisition of the image data transmitted from the receiving device when the image transfer start date and time comes, and causes, when the image processing start date and time comes, the image processing unit to perform specified image processing on the image data that the transfer has been started on the image transfer start date and time.

13. The inspection management system according to claim 12, wherein
the inspection management apparatus transmits, to the receiving device, information on a transfer target image among images captured by the capsule endoscope, and
the receiving device transfers, to the inspection management apparatus, the transfer target image based on the information.

14. The inspection management system according to claim 13, wherein
the information is information representing a type of organ, and
the receiving device includes a determination unit that determines, through image processing, a type of organ from the image data transmitted from the capsule endoscope.

15. The inspection management system according to claim 13, wherein
the information is information representing a type of organ, and
the receiving device includes a determination unit that determines a type of organ from the image data transmitted from the capsule endoscope, based on an elapsed time since introduction of the capsule endoscope into the subject.

16. The inspection management system according to claim 13, wherein
the information is information representing a period of time in which an observation target image is captured, and
the receiving device includes a determination unit that determines the observation target image from the image data transmitted from the capsule endoscope, based on an elapsed time since introduction of the capsule endoscope into the subject.

17. The inspection management system according to claim 13, wherein
the information is information representing an order that an observation target image is captured, and
the receiving device includes a determination unit that determines the observation target image from the image data transmitted from the capsule endoscope, based on an order that images are captured by the capsule endoscope.

18. The inspection management system according to claim 12, comprising a plurality of inspection management apparatuses, wherein
each of the plurality of inspection management apparatuses transmits identification information for identifying own inspection management apparatus to the receiving device, and
the receiving device transmits the image data to the inspection management apparatus corresponding to the identification information.

19. An inspection management method executed by an inspection management apparatus for managing an examination performed in a capsule endoscopic system including a receiving device that receives image data from a capsule endoscope and stores the image data, the method comprising:
receiving input of a first scheduled start date and time of the examination and a second scheduled start date and time of observation;
calculating an image transfer start date and time which is a date and time at which transfer of the image data from the receiving device to the inspection management apparatus is started, and calculating an image processing start date and time which is a date and time at which image processing is started on an image corresponding to the image data that the transfer has been started on the image transfer start date and time, based on the scheduled start date and time of the examination, the scheduled start date and time of observation, a predictive transfer time which is a first predictive time needed to transfer the image data from the receiving device to the inspection management apparatus and is stored in a storage unit in advance, and a predictive image processing time which is a second predictive time needed to perform image processing on the image data and set for each type of image processing and is stored in the storage unit in advance;
starting acquisition of the image data transmitted from the receiving device when the image transfer start date and time comes; and
performing, when the image processing start date and time comes, specified image processing on the image data that the transfer has been started on the image transfer start date and time.

20. A non-transitory computer readable recording medium on which an executable program is recorded, the program instructing a processor of a computer, which manages an examination performed in a capsule endoscopic system including a receiving device that receives image data from a capsule endoscope and stores the image data, to execute:
receiving input of a first scheduled start date and time of the examination and a second scheduled start date and time of observation;
calculating an image transfer start date and time which is a date and time at which transfer of the image data from the receiving device to the computer is started, and calculating an image processing start date and time which is a date and time at which image processing is started on an image corresponding to the image data that the transfer has been started on the image transfer start date and time, based on the scheduled start date and time of the examination, the scheduled start date and time of observation, a predictive transfer time which is a first predictive time needed to transfer the image data from the receiving device to the computer and is stored in a storage unit in advance, and a predictive image processing time which is a second predictive time needed to perform image processing on the image data and set for each type of image processing and is stored in the storage unit in advance;
starting acquisition of the image data transmitted from the receiving device when the image transfer start date and time comes; and
performing, when the image processing start date and time comes, specified image processing on the image data that the transfer has been started on the image transfer start date and time.

* * * * *